US012653940B2

(12) United States Patent
Pratt et al.

(10) Patent No.: US 12,653,940 B2
(45) Date of Patent: Jun. 16, 2026

(54) WOUND THERAPY SYSTEM WITH BLOCKAGE AND LEAK DETECTION

(71) Applicant: Solventum Intellectual Properties Company, Maplewood, MN (US)

(72) Inventors: Benjamin A. Pratt, Wimborne (GB); Justin Rice, San Antonio, TX (US)

(73) Assignee: Solventum Intellectual Properties Company, Maplewood, MN (US)

( * ) Notice: Subject to any disclaimer, the term of this patent is extended or adjusted under 35 U.S.C. 154(b) by 436 days.

(21) Appl. No.: 17/292,979

(22) PCT Filed: Nov. 8, 2019

(86) PCT No.: PCT/US2019/060590
§ 371 (c)(1),
(2) Date: May 11, 2021

(87) PCT Pub. No.: WO2020/102035
PCT Pub. Date: May 22, 2020

(65) Prior Publication Data
US 2022/0001100 A1     Jan. 6, 2022

Related U.S. Application Data

(60) Provisional application No. 62/767,177, filed on Nov. 14, 2018.

(51) Int. Cl.
A61M 1/00          (2006.01)

(52) U.S. Cl.
CPC .............. A61M 1/742 (2021.05); A61M 1/74 (2021.05); A61M 1/96 (2021.05); A61M 1/962 (2021.05);
(Continued)

(58) Field of Classification Search
CPC .......... A61M 1/742; A61M 1/74; A61M 1/96; A61M 1/962; A61M 1/98; A61M 1/982;
(Continued)

(56) References Cited

U.S. PATENT DOCUMENTS

| 1,355,846 | A | 10/1920 | Rannells |
| 2,547,758 | A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

International Search Report and Written Opinion on International Patent Application No. PCT/US2019/060590 dated Mar. 31, 2020 (14 pages).

(Continued)

*Primary Examiner* — Guy K Townsend
*Assistant Examiner* — Alessandro R Del Priore

(57)          ABSTRACT

A wound therapy system includes a single conduit fluidly connecting a wound site to a. removed fluid canister. A negative pressure circuit is defined by the wound site, the conduit, the removed fluid canister and tubing extending between the removed fluid canister and a pneumatic pump that applies negative pressure to the negative pressure circuit. A method of operating the wound therapy system includes profiling and benchmarking pressure decay within the negative pressure circuit against previous and/or expected pressure decay to identify any new or sudden anomalies that occur during the operation of the wound therapy system. The wound therapy system may additionally alert a user to such anomalous operation of the wound therapy system and/or identify and alert a user to an under- (Continued)

lying cause (e.g, blockage and/or leak, etc.) that is responsible for the anomalous readings.

14 Claims, 10 Drawing Sheets

(52) U.S. Cl.
CPC .............. *A61M 1/98* (2021.05); *A61M 1/982* (2021.05); *A61M 1/92* (2021.05); *A61M 2205/15* (2013.01); *A61M 2205/18* (2013.01); *A61M 2205/3344* (2013.01)

(58) Field of Classification Search
CPC ................ A61M 1/92; A61M 2205/15; A61M 2205/18; A61M 2205/3344; A61M 1/966; A61M 2205/3331; A61M 2205/50; A61M 2205/52
See application file for complete search history.

(56) References Cited

U.S. PATENT DOCUMENTS

| | | | |
|---|---|---|---|
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Flower, Jr. |
| 3,568,675 | A | 3/1971 | Harvey |
| 3,648,692 | A | 3/1972 | Wheeler |
| 3,682,180 | A | 8/1972 | McFarlane |
| 3,826,254 | A | 7/1974 | Mellor |
| 4,080,970 | A | 3/1978 | Miller |
| 4,096,853 | A | 6/1978 | Weigand |
| 4,139,004 | A | 2/1979 | Gonzalez, Jr. |
| 4,165,748 | A | 8/1979 | Johnson |
| 4,184,510 | A | 1/1980 | Murry et al. |
| 4,233,969 | A | 11/1980 | Lock et al. |
| 4,245,630 | A | 1/1981 | Lloyd et al. |
| 4,256,109 | A | 3/1981 | Nichols |
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,333,468 | A | 6/1982 | Geist |
| 4,373,519 | A | 2/1983 | Errede et al. |
| 4,382,441 | A | 5/1983 | Svedman |
| 4,392,853 | A | 7/1983 | Muto |
| 4,392,858 | A | 7/1983 | George et al. |
| 4,419,097 | A | 12/1983 | Rowland |
| 4,465,485 | A | 8/1984 | Kashmer et al. |
| 4,475,909 | A | 10/1984 | Eisenberg |
| 4,480,638 | A | 11/1984 | Schmid |
| 4,525,166 | A | 6/1985 | Leclerc |
| 4,525,374 | A | 6/1985 | Vaillancourt |
| 4,540,412 | A | 9/1985 | Van Overloop |
| 4,543,100 | A | 9/1985 | Brodsky |
| 4,548,202 | A | 10/1985 | Duncan |
| 4,551,139 | A | 11/1985 | Plaas et al. |
| 4,569,348 | A | 2/1986 | Hasslinger |
| 4,605,399 | A | 8/1986 | Weston et al. |
| 4,608,041 | A | 8/1986 | Nielsen |
| 4,640,688 | A | 2/1987 | Hauser |
| 4,655,754 | A | 4/1987 | Richmond et al. |
| 4,664,662 | A | 5/1987 | Webster |
| 4,710,165 | A | 12/1987 | McNeil et al. |
| 4,733,659 | A | 3/1988 | Edenbaum et al. |
| 4,743,232 | A | 5/1988 | Kruger |
| 4,758,220 | A | 7/1988 | Sundblom et al. |
| 4,787,888 | A | 11/1988 | Fox |
| 4,826,494 | A | 5/1989 | Richmond et al. |
| 4,838,883 | A | 6/1989 | Matsuura |
| 4,840,187 | A | 6/1989 | Brazier |

| | | | |
|---|---|---|---|
| 4,863,449 | A | 9/1989 | Therriault et al. |
| 4,872,450 | A | 10/1989 | Austad |
| 4,878,901 | A | 11/1989 | Sachse |
| 4,897,081 | A | 1/1990 | Poirier et al. |
| 4,906,233 | A | 3/1990 | Moriuchi et al. |
| 4,906,240 | A | 3/1990 | Reed et al. |
| 4,919,654 | A | 4/1990 | Kalt |
| 4,941,882 | A | 7/1990 | Ward et al. |
| 4,953,565 | A | 9/1990 | Tachibana et al. |
| 4,969,880 | A | 11/1990 | Zamierowski |
| 4,985,019 | A | 1/1991 | Michelson |
| 5,037,397 | A | 8/1991 | Kalt et al. |
| 5,086,170 | A | 2/1992 | Luheshi et al. |
| 5,092,858 | A | 3/1992 | Benson et al. |
| 5,100,396 | A | 3/1992 | Zamierowski |
| 5,134,994 | A | 8/1992 | Say |
| 5,149,331 | A | 9/1992 | Ferdman et al. |
| 5,167,613 | A | 12/1992 | Karami et al. |
| 5,176,663 | A | 1/1993 | Svedman et al. |
| 5,215,522 | A | 6/1993 | Page et al. |
| 5,232,453 | A | 8/1993 | Plass et al. |
| 5,261,893 | A | 11/1993 | Zamierowski |
| 5,278,100 | A | 1/1994 | Doan et al. |
| 5,279,550 | A | 1/1994 | Habib et al. |
| 5,298,015 | A | 3/1994 | Komatsuzaki et al. |
| 5,342,376 | A | 8/1994 | Ruff |
| 5,344,415 | A | 9/1994 | DeBusk et al. |
| 5,358,494 | A | 10/1994 | Svedman |
| 5,437,622 | A | 8/1995 | Carion |
| 5,437,651 | A | 8/1995 | Todd et al. |
| 5,527,293 | A | 6/1996 | Zamierowski |
| 5,549,584 | A | 8/1996 | Gross |
| 5,556,375 | A | 9/1996 | Ewall |
| 5,607,388 | A | 3/1997 | Ewall |
| 5,636,643 | A | 6/1997 | Argenta et al. |
| 5,645,081 | A | 7/1997 | Argenta et al. |
| 6,071,267 | A | 6/2000 | Zamierowski |
| 6,135,116 | A | 10/2000 | Vogel et al. |
| 6,241,747 | B1 | 6/2001 | Ruff |
| 6,287,316 | B1 | 9/2001 | Agarwal et al. |
| 6,345,623 | B1 | 2/2002 | Heaton et al. |
| 6,488,643 | B1 | 12/2002 | Tumey et al. |
| 6,493,568 | B1 | 12/2002 | Bell et al. |
| 6,553,998 | B2 | 4/2003 | Heaton et al. |
| 6,814,079 | B2 | 11/2004 | Heaton et al. |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2008/0071235 | A1* | 3/2008 | Locke .................... F16M 13/02 604/318 |
| 2011/0144540 | A1* | 6/2011 | Shen ...................... G16H 20/17 600/587 |
| 2012/0143114 | A1* | 6/2012 | Locke ............... A61F 13/00042 604/319 |
| 2013/0144227 | A1* | 6/2013 | Locke .................... A61M 1/98 604/319 |
| 2014/0299544 | A1* | 10/2014 | Wilt ................... A61M 60/427 417/474 |
| 2016/0101227 | A1* | 4/2016 | Norris ................... A61M 1/155 604/29 |
| 2016/0239025 | A1* | 8/2016 | van der Merwe .. F16K 31/0627 |
| 2016/0287166 | A1* | 10/2016 | Tran ........................ A61B 5/74 |
| 2017/0014606 | A1* | 1/2017 | Locke .................... A61M 1/96 |
| 2020/0121833 | A9* | 4/2020 | Askem ................ B29C 65/7805 |
| 2021/0121609 | A1* | 4/2021 | Gregory ................. A61M 1/98 |
| 2021/0290837 | A1* | 9/2021 | Brandolini ............ A61M 1/964 |

FOREIGN PATENT DOCUMENTS

| | | | |
|---|---|---|---|
| AU | 755496 | B2 | 12/2002 |
| CA | 2005436 | A1 | 6/1990 |
| DE | 2640413 | A1 | 3/1978 |
| DE | 4306478 | A1 | 9/1994 |
| DE | 29504378 | U1 | 9/1995 |
| EP | 0100148 | A1 | 2/1984 |
| EP | 0117632 | A2 | 9/1984 |
| EP | 161865 | A2 | 11/1985 |

(56) References Cited

FOREIGN PATENT DOCUMENTS

| EP | 358302 | A2 | 3/1990 | |
| EP | 1018967 | A1 | 7/2000 | |
| EP | 2 782 615 | A1 | 10/2014 | |
| EP | 3187204 | A1 * | 7/2017 | ....... A61F 13/00068 |
| GB | 692578 | A | 6/1953 | |
| GB | 2195255 | A | 4/1988 | |
| GB | 2197789 | A | 6/1988 | |
| GB | 2220357 | A | 1/1990 | |
| GB | 2235877 | A | 3/1991 | |
| GB | 2329127 | A | 3/1999 | |
| GB | 2333965 | A | 8/1999 | |
| JP | 4129536 | B2 | 8/2008 | |
| SG | 71559 | | 4/2002 | |
| WO | 80/02182 | A1 | 10/1980 | |
| WO | 8704626 | A1 | 8/1987 | |
| WO | 90010424 | A1 | 9/1990 | |
| WO | 93009727 | A1 | 5/1993 | |
| WO | 94020041 | A1 | 9/1994 | |
| WO | 9605873 | A1 | 2/1996 | |
| WO | 97/18007 | A1 | 5/1997 | |
| WO | 9913793 | A1 | 3/1999 | |
| WO | WO-2017/044138 | A1 | 3/2017 | |

OTHER PUBLICATIONS

Louis C. Argenta, Md and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.

Chariker, Mark E., M.D., et al; "Effective Management of incisional and cutaneous fistulae with closed suction wound drainage"; Contemporary Surgery, vol. 34, Jun. 1989, pp. 59-63.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96.

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A.C.® Therapy Clinical Guidelines: A Reference Source for Clinicians; Jul. 2007.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, Md., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164.

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

(56)     References Cited

OTHER PUBLICATIONS

V.A. Solovev et al., Guidelines, The Method of Treatment of
Immature External Fistulas in the Upper Gastrointestinal Tract,
editor-in-chief Prov. V.I. Parahonyak (S.M. Kirov Gorky State
Medical Institute, Gorky, U.S.S.R. 1987) ("Solovev Guidelines").
V.A. Solovev, Dissertation Abstract, Treatment and Prevention of
Suture Failures after Gastric Resection (S.M. Kirov Gorky State
Medical Institute, Gorky, U.S.S.R. 1988) ("Solovev Abstract").

* cited by examiner

Verification Loop 700

Leak Loop 800

Blockage Loop 900

902
Attain Target Pressure

904
Wait Predetermined Time Interval

906
Open Valve

908
Observe 1st Dynamic Pressure Response 910
1st Dynamic Pressure Response ≈
Expected Dynamic Pressue Response?

Yes

No

912
Continue
Operation of
NPWT System

914
Run Issue
Identification Loop
(See FIG. 10)

Issue Identification Loop 1000

WOUND THERAPY SYSTEM WITH BLOCKAGE AND LEAK DETECTION

CROSS-REFERENCE TO RELATED APPLICATIONS

The present application is a US national phase application under 35 USC § 371 of International Application No. PCT/US2019/060590, filed on Nov. 8, 2019, which claims the benefit of priority to U.S. Provisional Application No. 62/767,177, entitled "Wound Therapy System with Blockage and Leak Detection" filed on Nov. 14, 2018, which are hereby incorporated herein by reference in their entireties.

BACKGROUND

The present disclosure relates generally to a wound therapy system, and more particularly to a wound therapy system that provides negative pressure wound therapy. Negative pressure wound therapy (NPWT) is a type of wound therapy that involves applying a negative pressure to a wound site to promote wound healing. Some wound treatment systems apply negative pressure to a wound using a pump to generate the negative pressure and flow required.

The benefit of NPWT is typically dependent on the ability to apply and maintain the wound site at a predetermined negative pressure. As will be understood, a blockage and/or leak in the therapy system which interferes with or prevents the predetermined negative pressure from being applied to and/or sustained at the wound site negatively impacts the ability of the therapy system to effective treat the wound.

Some existing therapy systems incorporate a blockage detecting feature in an attempt to prevent such blockages from impacting NPWT treatment. However, such existing therapy systems typically rely on specific additional components (e.g. additional pressure sensors, secondary pressure monitoring conduits, etc.) being incorporated into the therapy system to provide the therapy system blockage detection functionality.

SUMMARY

One implementation of the present disclosure is a wound therapy system that includes a canister, a conduit, a pump, a pressure indicator and a controller. The canister is configured to contain fluid removed from a wound site. The conduit has a first end coupled to the canister and a second end operably coupled to the wound site. An interior volume of the canister and an interior volume of the conduit define a negative pressure circuit. The pump is fluidly operably coupled to the wound site via the conduit and is configured to apply negative pressure to the wound site via the negative pressure circuit. The pressure indicator is configured to indicate a pressure within the negative pressure circuit. The controller is configured to store a baseline pressure decay curve representative of a change in pressure within the negative pressure circuit from a first negative pressure to a predetermined threshold pressure over a first period of time; generate a second pressure decay curve by operating the pump to apply a second applied negative pressure equal to the first negative pressure to the negative pressure circuit and measure a change in pressure over a second period of time within the negative pressure circuit during which the pressure within the negative pressure circuit increases from the second applied negative pressure to the threshold pressure; compare the second pressure decay curve to the baseline pressure decay curve; and generate an alert in response to detecting that a difference between the second pressure decay curve and the baseline pressure decay curve exceeds a predetermined first variance threshold.

In some embodiments, in response to generating the alert, the controller is further configured to generate a third pressure decay curve by operating the pump to apply a third applied negative pressure equal to the first negative pressure to the negative pressure circuit and measure a change in pressure over a third time period within the negative pressure circuit during which the pressure within the negative pressure circuit increases from the third applied negative pressure to the threshold pressure; and compare the third pressure decay curve to the second pressure decay curve.

In some embodiments, the controller is further configured to generate a blockage alarm in response to detecting that the third pressure decay curve is substantially the same as the second pressure decay curve. In some embodiments, the controller is further configured to generate a leakage alarm in response to detecting that a difference between the third pressure decay curve and the second pressure decay curve exceeds a predetermined second variance threshold.

In some embodiments, in response to detecting that the second pressure decay curve is substantially the same as the baseline pressure decay curve, the controller is further configured to, following a predetermined time interval, generate a third pressure decay curve by operating the pump to apply a third applied negative pressure equal to the first negative pressure to the negative pressure circuit and measure a change in pressure over a third time period within the negative pressure circuit during which the pressure within the negative pressure circuit increases from the third applied negative pressure to the threshold pressure; and compare the third pressure decay curve to the baseline pressure decay curve.

In some embodiments, the baseline pressure decay curve stored by the controller is generated based on measuring pressure decay within the negative pressure circuit prior to an initial use of the wound therapy system to provide negative pressure therapy to the wound site.

In some embodiments, the wound therapy system further includes a calibrated leak in fluid communication with the negative pressure circuit. The calibrated leak is configured to allow ambient air to flow into the negative pressure circuit at a known flow rate and increase in pressure within the negative pressure circuit.

In some embodiments, the detected difference between the second pressure decay curve and the baseline pressure decay curve includes at least one of a difference between a slope of the baseline pressure decay curve and a slope of the second pressure decay curve and a difference between the first period of the time and the second period of time. In some embodiments, the first variance threshold is between approximately 5% and approximately 15%. In some embodiments, the detected difference between the third pressure decay curve and the second pressure decay curve includes at least one of a difference between a slope of the third pressure decay curve and a slope of the second pressure decay curve and a difference between the third period of the time and the second period of time. In some embodiments, the second variance threshold is between approximately 5% and approximately 15%. In some embodiments, the detected difference between the second pressure decay curve and the baseline pressure decay curve includes at least one of a difference between a slope of the baseline pressure decay curve and a slope of the second pressure decay curve and a difference between the first period of the time and the second period of time. In some embodiments, the first variance threshold is between approximately 5% and approximately 15%. In some embodiments, the detected difference between the third pressure decay curve and the second pressure decay curve includes at least one of a difference between a slope of the third pressure decay curve and a slope of the second pressure decay curve and a difference between the third period of the time and the second period of time. In some embodiments, the second variance threshold is between approximately 5% and approximately 15%.

In some embodiments, the interior volume of the conduit is defined by a single lumen. In some embodiments, the conduit defines the only fluid path between the canister and the wound site. In some embodiments, the baseline pressure decay curve stored by the controller includes a plurality of volume-specific baseline pressure decay curves, each of the volume-specific baseline pressure decay curves being representative of a change in pressure within a negative pressure circuit defined by a specific volume. The controller is further configured to determine a volume of the negative pressure circuit. The baseline pressure decay curve to which the second decay curve is compared includes a volume-specific baseline pressure decay curve corresponding to the determined volume of the negative pressure circuit.

In some embodiments, the volume of the negative pressure circuit is determined based on an identification by the controller of the interior volume of the canister. In some embodiments, the volume of the negative pressure circuit is further determined based on an identification by the controller of an amount of fluid that has been instilled to the wound site.

One implementation of the present disclosure is a controller for a wound therapy system. The controller is configured to store a baseline pressure decay curve for a negative pressure circuit of a wound therapy device defined by an interior volume of a canister and an interior volume of a conduit extending between the canister and a wound site, the baseline pressure decay curve representative of a change in pressure within the negative pressure circuit from a first negative pressure to a second threshold pressure over a first period of time; generate a second pressure decay curve by operating a pump of the wound therapy device to apply a second applied negative pressure equal to the first negative pressure to the negative pressure circuit and measure a change in pressure over a second period of time within the negative pressure circuit during which the pressure within the negative pressure circuit increases from the second applied negative pressure to the threshold pressure; compare the second pressure decay curve to the baseline pressure decay curve; and generate an alert in response to detecting that a difference between the second pressure decay curve and the baseline pressure decay curve exceeds a predetermined first variance threshold.

In some embodiments, in response to generating the alert, the controller is further configured to generate a third pressure decay curve by operating the pump to apply a third applied negative pressure equal to the first negative pressure to the negative pressure circuit and measure a change in pressure over a third time period within the negative pressure circuit during which the pressure within the negative pressure circuit increases from the third applied negative pressure to the threshold pressure; and compare the third pressure decay curve to the second pressure decay curve.

In some embodiments, the controller is further configured to generate a blockage alarm in response to detecting that the third pressure decay curve is substantially the same as the second pressure decay curve. In some embodiments, the controller is further configured to generate a leakage alarm in response to detecting that a difference between the third pressure decay curve and the second pressure decay curve exceeds a predetermined second variance threshold.

In some embodiments, in response to detecting that the second pressure decay curve is substantially the same as the baseline pressure decay curve, the controller is further configured to, following a predetermined time interval: generate a third pressure decay curve by operating the pump to apply a third applied negative pressure equal to the first negative pressure to the negative pressure circuit and measure a change in pressure over a third time period within the negative pressure circuit during which the pressure within the negative pressure circuit increases from the third applied negative pressure to the threshold pressure; and compare the third pressure decay curve to the baseline pressure decay curve.

In some embodiments, the baseline pressure decay curve stored by the controller is generated based on pressure decay measured within the negative pressure circuit prior to an initial use of the wound therapy system to provide negative pressure therapy to the wound site. In some embodiments, the detected difference between the second pressure decay curve and the baseline pressure decay curve includes at least one of a difference between a slope of the baseline pressure decay curve and a slope of the second pressure decay curve and a difference between the first period of the time and the second period of time. In some embodiments, the first variance threshold is between approximately 5% and approximately 15%.

In some embodiments, the detected difference between the third pressure decay curve and the second pressure decay curve includes at least one of a difference between a slope of the third pressure decay curve and a slope of the second pressure decay curve and a difference between the third period of the time and the second period of time. In some embodiments, the second variance threshold is between approximately 5% and approximately 15%. In some embodiments, the detected difference between the second pressure decay curve and the baseline pressure decay curve includes at least one of a difference between a slope of the baseline pressure decay curve and a slope of the second pressure decay curve and a difference between the first period of the time and the second period of time. In some embodiments, the first variance threshold is between approximately 5% and approximately 15%.

In some embodiments, the detected difference between the third pressure decay curve and the second pressure decay curve includes at least one of a difference between a slope of the third pressure decay curve and a slope of the second pressure decay curve and a difference between the third period of the time and the second period of time. In some embodiments, the second variance threshold is between approximately 5% and approximately 15%. In some embodiments, the baseline pressure decay curve stored by the controller includes a plurality of volume-specific baseline pressure decay curves, each of the volume-specific baseline pressure decay curves being representative of a change in pressure within a negative pressure circuit defined by a specific volume. The controller is further configured to determine a volume of the negative pressure circuit. The baseline pressure decay curve to which the second decay curve is compared includes a volume-specific baseline pressure decay curve corresponding to the determined volume of the negative pressure circuit.

In some embodiments, the volume of the negative pressure circuit is determined based on an identification by the controller of the interior volume of the canister. In some embodiments, volume of the negative pressure circuit is further determined based on an identification by the controller of an amount of fluid that has been instilled to the wound site.

One implementation of the present disclosure is a non-transitory computer readable medium comprising instructions which, when executed by a controller are configured to cause the controller to instruct a pump of a wound therapy device to apply a first applied negative pressure to a negative pressure circuit of a wound therapy device defined by an interior volume of a canister and an interior volume of a conduit extending between the canister and a wound site; generate a first pressure decay curve based on a detected a change in pressure over a first period of time within the negative pressure circuit during which the pressure within the negative pressure circuit increases from the first applied negative pressure to the threshold pressure; compare the first pressure decay curve to a baseline pressure decay curve generated prior to an initial operation of the wound therapy device, the baseline pressure decay curve being representative of a change in pressure within the negative pressure circuit from an applied negative pressure equal to the to the first applied negative pressure to the threshold pressure over an initial period of time; and generate an alert in response to detecting that a difference between the first pressure decay curve and the baseline pressure decay curve exceeds a predetermined first variance threshold.

In some embodiments, the code, when executed by the controller, is further configured to cause the controller to: in response to generating the alert, instruct the pump to apply a second applied negative pressure equal to the first negative pressure to the negative pressure circuit; generate a second pressure decay curve based on a detected change in pressure over a second time period within the negative pressure circuit during which the pressure within the negative pressure circuit increases from the second applied negative pressure to the threshold pressure; and compare the second pressure decay curve to the first pressure decay curve.

In some embodiments, the code, when executed by the controller, is further configured to cause the controller to generate a blockage alarm in response to detecting that the second pressure decay curve is substantially the same as the first pressure decay curve. In some embodiments, the code, when executed by the controller, is further configured to cause the controller to generate a leakage alarm in response to detecting that a difference between the third pressure decay curve and the second pressure decay curve exceeds a predetermined second variance threshold.

In some embodiments, the code, when executed by the controller, is further configured to cause the controller, following a predetermined time interval and in response to detecting that the second pressure decay curve is substantially the same as the baseline pressure decay curve, to: instruct the pump to apply a third applied negative pressure equal to the first negative pressure to the negative pressure circuit; generate a third pressure decay curved based on a detected change in pressure over a third time period within the negative pressure circuit during which the pressure within the negative pressure circuit increases from the third applied negative pressure to the threshold pressure; and compare the third pressure decay curve to the baseline pressure decay curve.

One implementation of the present disclosure is method for detecting a blockage or a leak in a wound therapy system comprising operating a pump to apply a first applied negative pressure to a negative pressure circuit of a wound therapy system defined by an interior volume of a canister and interior volume of a conduit extending between the canister and a wound site. A first pressure decay curve is generated representative of a change in pressure within the negative pressure circuit over a first period of time during which a pressure within the negative pressure circuit increases from the first applied negative pressure to a predetermined threshold pressure. The first pressure decay curve is compared to a baseline pressure decay curve. An alert is generated in response to detecting that a difference between the first pressure decay curve and the baseline pressure decay curve exceeds a predetermined first variance threshold.

In some embodiments, the baseline pressure decay curve is generated prior to an initial use of the wound therapy system. The baseline pressure decay curve is representative of a change in pressure within the negative pressure circuit over an initial period of time during which a pressure within the negative pressure circuit increases from the first applied negative pressure to the threshold pressure.

In some embodiments, immediately following the generation of the alert, the pump is operated to apply the first negative pressure to the negative pressure circuit. A second pressure decay curve is generated representative of a change in pressure over a second time period within the negative pressure circuit during which the pressure within the negative pressure circuit increases from the first applied negative pressure to the threshold pressure. The second pressure decay curve is compared to the first pressure decay curve.

In some embodiments, a blockage alarm is generated in response to detecting that the second pressure decay curve is substantially the same as the first pressure decay curve. In some embodiments, a leakage alarm is generated in response to detecting that a difference between the second pressure decay curve and the first pressure decay curve exceeds a predetermined second variance threshold.

In some embodiments, the pump is operated to apply a second applied negative pressure equal to the first negative pressure to the negative pressure circuit in response to detecting that the first pressure decay curve is substantially the same as the baseline pressure decay curve. A second pressure decay curve is generated representative of a change in pressure over a second time period within the negative pressure circuit during which the pressure within the negative pressure circuit increases from the second applied negative pressure to the threshold pressure. The second pressure decay curve is compared to the baseline pressure decay curve.

In some embodiments, a calibrated leak allows ambient air to flow into the negative pressure circuit at a known flow rate is provided to increase pressure within the negative pressure circuit. In some embodiments, the baseline pressure decay curve includes a plurality of volume-specific baseline pressure decay curves, each of the volume-specific baseline pressure decay curves being representative of a change in pressure within a negative pressure circuit defined by a specific volume over an initial period of time during which a pressure within the negative pressure circuit increases from the first applied negative pressure to the threshold pressure.

In some embodiments, the first pressure decay curve is compared to a volume-specific baseline pressure decay curve corresponding to the determined volume of the negative pressure circuit. In some embodiments, the volume of the negative pressure circuit is determined based on an interior volume of the canister. In some embodiments, the volume of the negative pressure circuit is further determined based on an amount of fluid that has been instilled to the wound site.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

DETAILED DESCRIPTION

Referring generally to the FIGURES, a wound therapy system is shown, according to various exemplary embodiments. The wound therapy system may include a therapy device and a wound dressing. The NPWT systems and methods described herein advantageously include blockage and/or leak detecting capabilities, while minimizing the structural components that define the NPWT system. In contrast to existing blockage-detecting NPWT treatment devices, the NPWT systems and methods described herein do not require the incorporation of additional structural component to achieved blockage detection function, but rather allow for blockages and/or leaks to be detected using a NPWT system defined by only a single conduit extending between the NPWT therapy device and wound site and only a single pressure sensor. Accordingly, as will be understood, the wound therapy system and methods disclosed herein provide a cost effective solution to detecting blockages and/or leaks within and system.

Wound Therapy System

Figure 1:
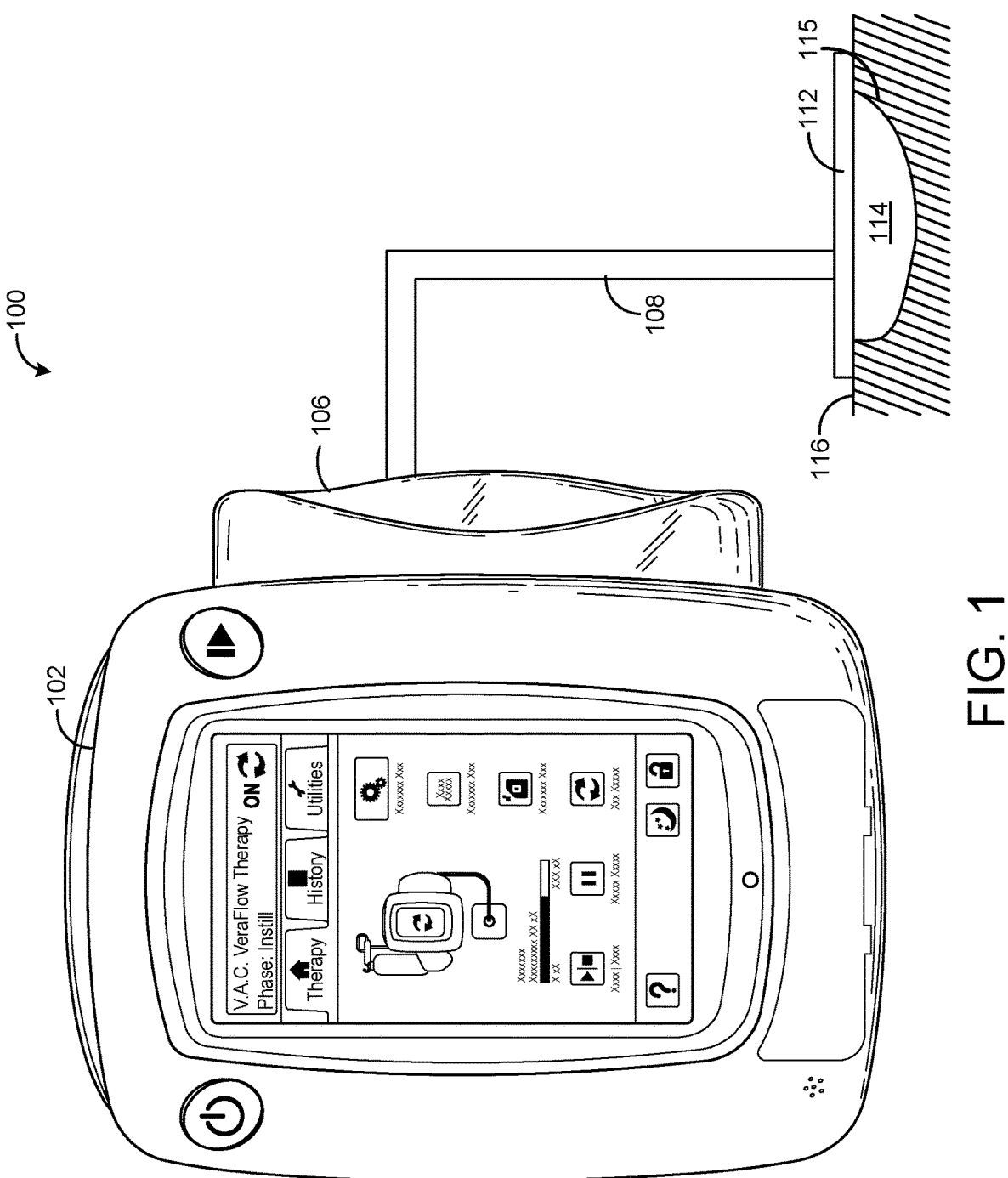
FIG. 1 is a block diagram of a wound therapy system including a therapy device coupled to a wound dressing, according to an exemplary embodiment.
Figure 2:
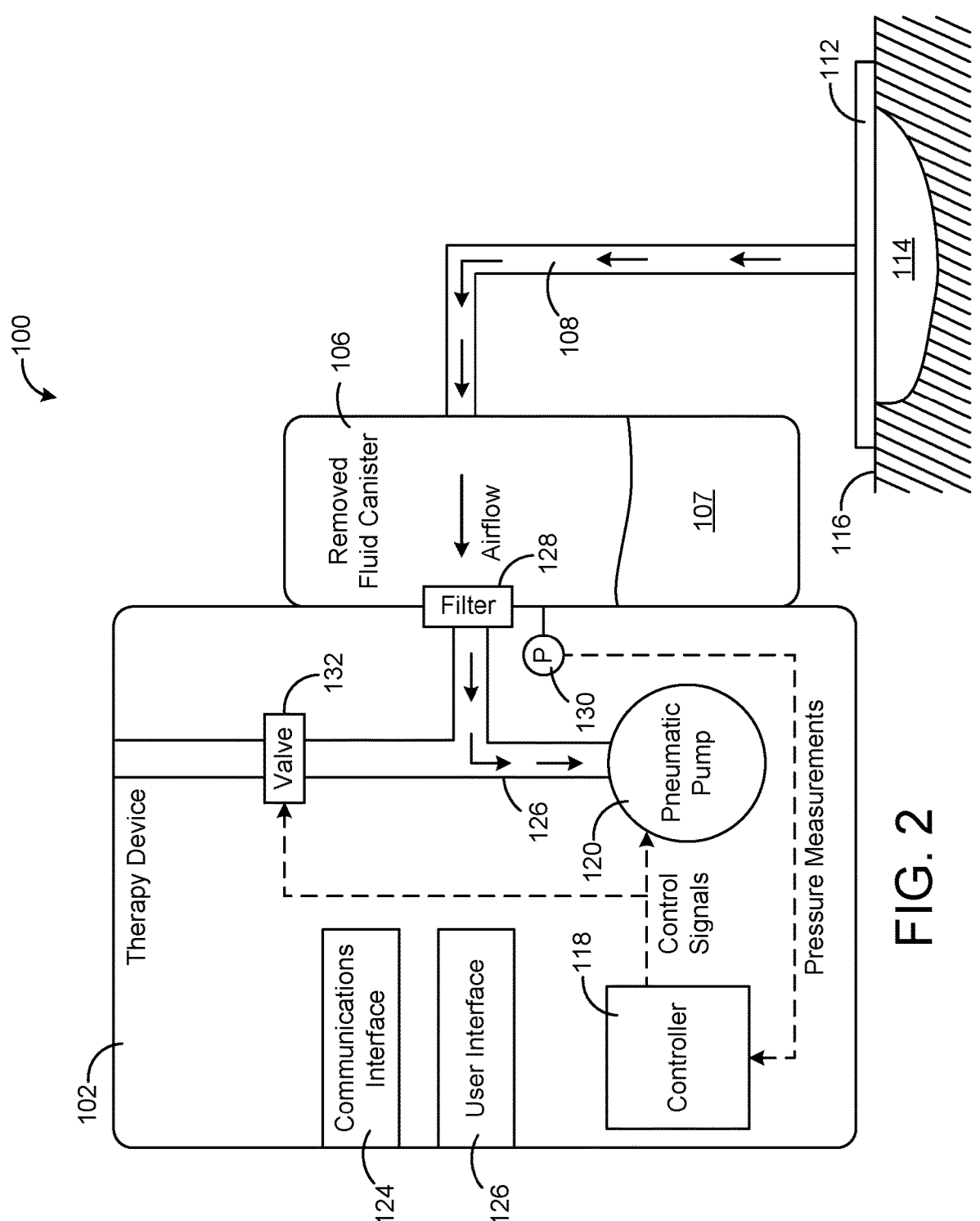
FIG. 2 is a block diagram illustrating the therapy device of FIG. 1 in greater detail and illustrating the operation of the therapy device to reduce pressure within a negative pressure circuit, according to an exemplary embodiment.
Figure 3:
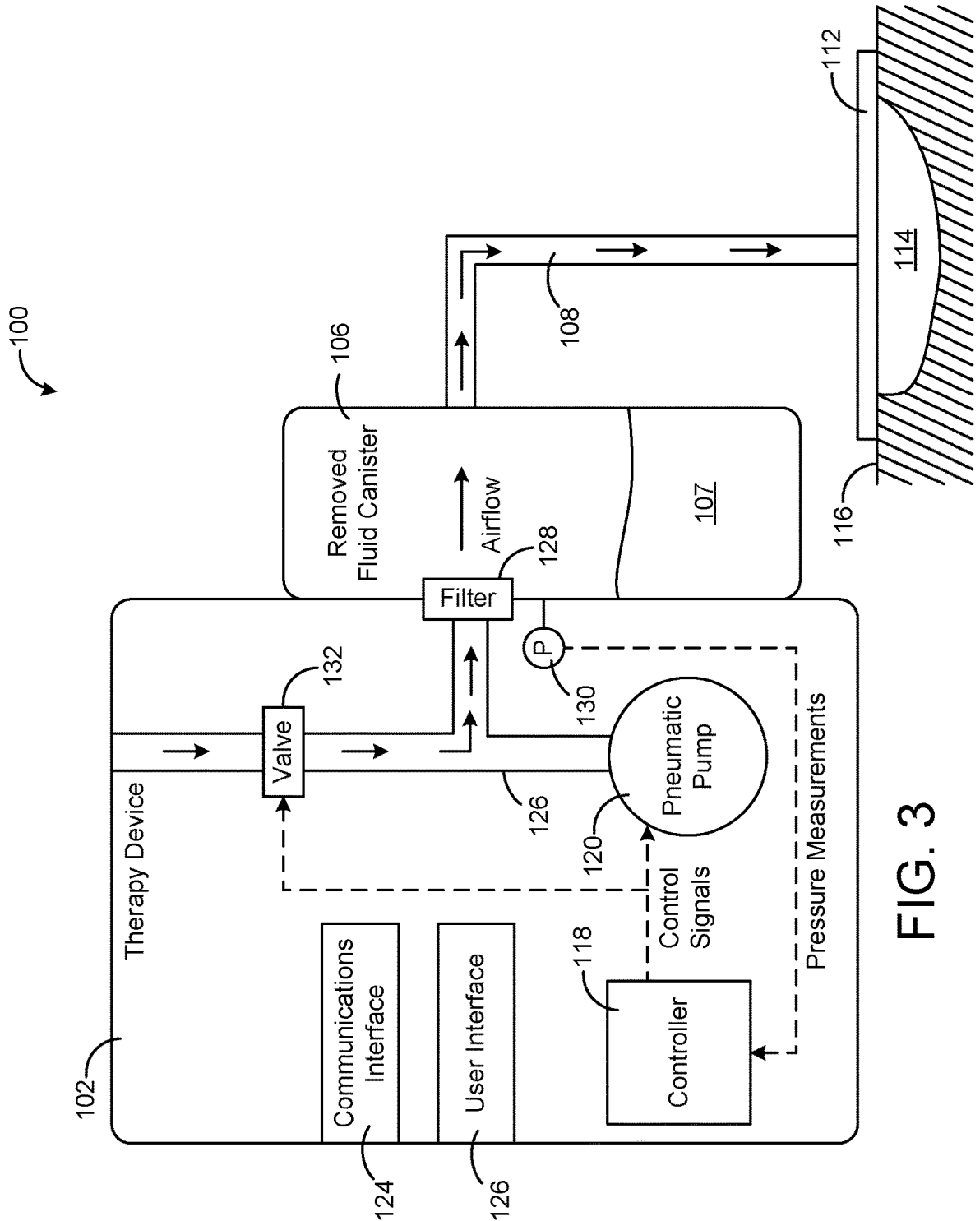
FIG. 3 is a block diagram illustrating the operation of the therapy device of FIG. 1 to vent the negative pressure circuit, according to an exemplary embodiment.

Referring to FIGS. 1-3, a negative pressure wound therapy (NPWT) system 100 is shown according to an exemplary embodiment. NPWT system 100 is shown to include a therapy device 102 fluidly connected to a wound dressing 112 via a conduit 108. Wound dressing 112 may be adhered or sealed to a patient's skin 116 surrounding a wound 115. Several examples of wound dressings 112 which can be used in combination with NPWT system 100 are described in detail in U.S. Pat. No. 7,651,484 granted Jan. 26, 2010, U.S. Pat. No. 8,394,081 granted Mar. 12, 2013, U.S. patent application Ser. No. 14/087,418 filed Nov. 22, 2013, and U.S. Provisional Patent Application No. 62/650, 132 filed Mar. 29, 2018. The entire disclosure of each of these patents and patent applications is incorporated by reference herein.

Therapy device 102 can be configured to provide negative pressure wound therapy by reducing the pressure at wound site 114. Therapy device 102 can draw a vacuum at wound site 114 (relative to atmospheric pressure) by removing fluids 107 such as wound exudate, air, and other fluids from wound 115. Wound exudate may include fluid that filters from a patient's circulatory system into lesions or areas of inflammation. For example, wound exudate may include water and dissolved solutes such as blood, plasma proteins, white blood cells, platelets, and red blood cells. Other fluids removed from wound 115 may include instillation fluid previously delivered to wound 115. Instillation fluid can include, for example, a cleansing fluid, a prescribed fluid, a medicated fluid, an antibiotic fluid, or any other type of fluid which can be delivered to wound 115 during wound treatment. In some embodiments, therapy device 102 is configured to deliver instillation fluid to wound 115, as described in U.S. Provisional Patent Application No. 62/650,132 filed Mar. 29, 2018, the entire disclosure of which is incorporated by reference herein.

Fluids 107 removed from wound 115 pass through conduit 108 and are collected in a removed fluid canister 106. Conduit 108 may have a first end coupled to canister 106 and a second end coupled to the wound site (e.g., wound dressing 112). Canister 106 may be a component of therapy device 102 configured to collect wound exudate and other fluids 107 removed from wound 115. In some embodiments, canister 106 is detachable from therapy device 102 to allow canister 106 to be emptied and replaced as needed. A lower portion of canister 106 may be filled with wound exudate and other fluids 107 removed from wound 115, whereas an upper portion of canister 106 may be filled with air. As will be understood, over the course of treatment, as negative pressure is applied to the wound 115 and wound exudate and other fluids 107 are removed from the wound site 114, the relative volume of wound exudate and other fluid 107 in the canister increases and the volume of the air in the canister 106 decreases.

Therapy device 102 can be configured to draw a vacuum within canister 106 by pumping air out of canister 106. The reduced pressure within canister 106 can be translated to wound dressing 112 and wound 115 via conduit 108 such that wound dressing 112 and wound 115 are maintained at substantially the same pressure as canister 106.

Referring to FIG. 2, a block diagram illustrating therapy device 102 in greater detail are shown, according to an exemplary embodiment. Therapy device 102 is shown to include a pneumatic pump 120, a relief valve 132, a filter 128, and a controller 118. Pump 120 can be fluidly coupled to canister 106 (e.g., via conduit 126) and can be configured to draw a vacuum within canister 106 by pumping air out of canister 106. In some embodiments, pump 120 is configured to operate in both a forward direction and a reverse direction. For example, pump 120 can operate in the forward direction to pump air out of canister 106 and decrease the pressure within canister 106. Pump 120 can operate in the reverse direction to pump air into canister 106 and increase the pressure within canister 106. Pump 120 can be controlled by controller 118, described in greater detail below.

Filter 128 can be positioned between canister 106 and pump 120 (e.g., along conduit 126) such that the air pumped out of canister 106 passes through filter 128. Filter 128 can be configured to prevent liquid or solid particles from entering conduit 126 and reaching pump 120. Filter 128 may include, for example, a bacterial filter that is hydrophobic and/or lipophilic such that aqueous and/or oily liquids will bead on the surface of filter 128. Pump 120 can be configured to provide sufficient airflow through filter 128 that the pressure drop across filter 128 is not substantial (e.g., such that the pressure drop will not substantially interfere with the application of negative pressure to wound 115 from therapy device 102).

Valve 132 can be fluidly connected with pump 120 and filter 128 via conduit 126. In some embodiments, valve 132 is configured to control airflow between conduit 126 and the environment around therapy device 102. For example, valve 132 can be opened to allow airflow into conduit 126, and closed to prevent airflow into conduit 126. Valve 132 can be opened and closed by controller 118. The negative pressure circuit may include any component of NPWT system 100 that can be maintained at a negative pressure when performing negative pressure wound therapy (e.g., conduit 126, canister 106, conduit 108, wound dressing 112, and/or wound 115).

In some embodiments, therapy device 102 includes one or more sensors. For example, therapy device 102 is shown to include a pressure sensor 130 configured to measure the pressure within canister 106 and/or the pressure at wound dressing 112 or wound 115. As noted above, according to various embodiments, the therapy device is defined by and includes only a single sensor. Pressure measurements recorded by pressure sensor 130 can be communicated to controller 118. Controller 118 uses the pressure measurements to ensure that wound 115 is maintained at negative pressure. For example, controller 118 can activate pump 120 in response to the pressure measurement from pressure sensor 130 exceeding a negative pressure setpoint in order to reduce the pressure at wound 115.

Controller

Figure 4:
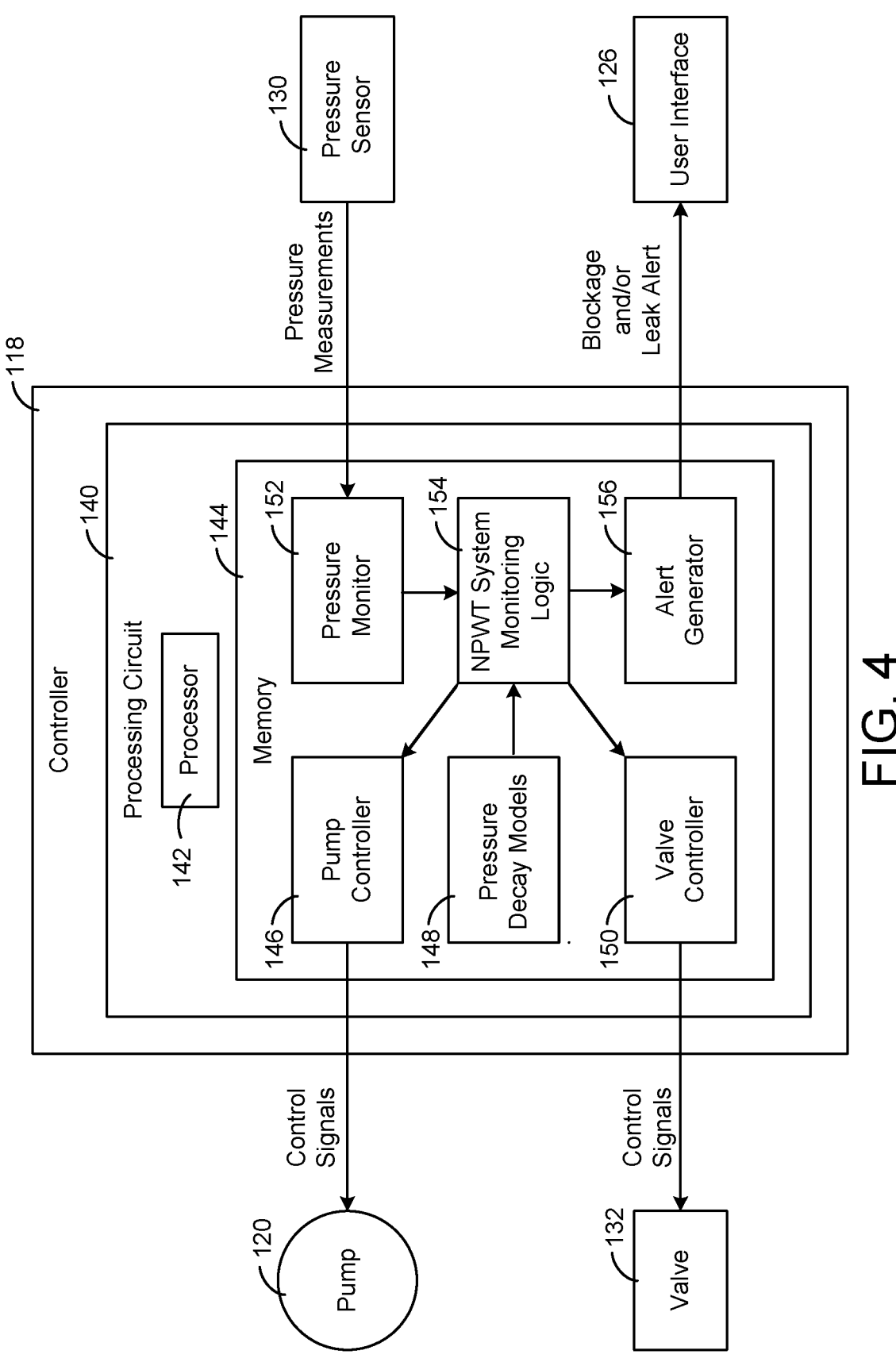
FIG. 4 is a block diagram illustrating a controller of the wound therapy device of FIG. 1 in greater detail, according to an exemplary embodiment.

Referring to FIG. 4, controller 118 is shown to include a processor 142 and memory 144. Processor 142 may be a general purpose or specific purpose processor, an application specific integrated circuit (ASIC), one or more field programmable gate arrays (FPGAs), a group of processing components, or other suitable processing components. Processor 142 is configured to execute computer code or instructions stored in memory 144 or received from other computer readable media (e.g., CDROM, network storage, a remote server, etc.). According to various embodiments, the processor 142 is configured to operate the controller to automatically effectuate the methods of detecting blockages and/or leaks disclosed herein.

Memory 144 may include one or more devices (e.g., memory units, memory devices, storage devices, etc.) for storing data and/or computer code for completing and/or facilitating the various processes described in the present disclosure. Memory 144 may include random access memory (RAM), read-only memory (ROM), hard drive storage, temporary storage, non-volatile memory, flash memory, optical memory, or any other suitable memory for storing software objects and/or computer instructions. Memory 144 may include database components, object code components, script components, or any other type of information structure for supporting the various activities and information structures described in the present disclosure. Memory 144 may be communicably connected to processor 142 and may include computer code for executing (e.g., by processor 142) one or more processes described herein. When processor 142 executes instructions stored in memory 144, processor 142 generally configures controller 118 to complete such activities. According to various embodiments, the memory 144 is configured to store the NPWT system monitoring logic 154, which, when executed, is configured to operate the controller to automatically effectuate the methods of detecting blockages and/or leaks disclosed using verification loop 700, leak loop 800, blockage loop 900 and/or issue identification loop 1000 as discussed in more detail below with reference to FIGS. 7-10. According to various embodiments, the memory 144 additionally stores model pressure decay model data 148 that is used by the NPWT System monitoring logic 154 to detect blockages and/or leaks during operation of the NPWT system 100.

Controller 118 is shown to include a pump controller 146 and a valve controller 150. Pump controller 146 can be configured to operate pump 120 by generating and providing control signals to pump 120. The control signals provided to pump 120 can cause pump 120 to activate, deactivate, or achieve a variable capacity or speed (e.g., operate at half speed, operate at full speed, etc.). Similarly, valve controller 150 can be configured to operate valve 132 by generating and providing control signals to valve 132. The control signals provided to valve 132 can cause valve 132 to open, close, or achieve a specified intermediate position (e.g., one-third open, half open, etc.). As will be understood, according to various embodiments, NPWT system monitoring logic 154 may utilize the pump controller 146 and/or valve controller 150 are used to effectuate the operation of the pump 120 and/or the opening/closing of the valve 132 during any or all of the verification loop 700, leak loop 800, blockage loop 900 and/or issue identification loop 1000 described herein.

In some embodiments, pump controller 146 uses input from a canister sensor configured to detect whether canister 106 is present. Pump controller 146 can be configured to activate pump 120 only when canister 106 is present. For example, pump controller 146 can check whether canister 106 is present and can activate pump 120 in response to a determination that canister 106 is present. However, if canister 106 is not present, pump controller 146 may prevent pump 120 from activating.

Controller 118 is shown to include a pressure monitor 152. Pressure monitor 152 can be configured to monitor the pressure within canister 106 and/or the pressure within wound dressing 112 or wound site 114 using feedback from pressure sensor 130. For example, pressure sensor 130 may provide pressure measurements to pressure monitor 152. Pressure monitor 152 can use the pressure measurements to determine the pressure within canister 106 and/or the pressure within wound dressing 112 or wound site 114 in real-time. As will be understood, according to various embodiments, the pressure measurement values relied upon in performing any of the verification loop 700, leak loop 800, blockage loop 900 and/or issue identification loop 1000 may be pressure measurements provided by the pressure monitor 152.

In some embodiments, therapy device 102 includes a data communications interface 124 (e.g., a USB port, a wireless transceiver, etc.) configured to receive and transmit data. Communications interface 124 may include wired or wireless communications interfaces (e.g., jacks, antennas, transmitters, receivers, transceivers, wire terminals, etc.) for conducting data communications external systems or devices. In various embodiments, the communications may be direct (e.g., local wired or wireless communications) or via a communications network (e.g., a WAN, the Internet, a cellular network, etc.). For example, communications interface 124 can include a USB port or an Ethernet card and port for sending and receiving data via an Ethernet-based communications link or network. In another example, communications interface 124 can include a Wi-Fi transceiver for communicating via a wireless communications network or cellular or mobile phone communications transceivers.

In some embodiments, therapy device 102 includes a user interface 148. User interface 148 may include one or more buttons, dials, sliders, keys, or other input devices configured to receive input from a user. User interface 148 may also include one or more display devices (e.g., LEDs. LCD displays, etc.), speakers, tactile feedback devices, or other output devices configured to provide information to a user. In some embodiments, the pressure measurements recorded by pressure sensor 130 are presented to a user via user interface 148. User interface 148 can also display alerts generated by controller 118. For example, alert generator 156 can generate a "blockage detected" and/or a "leakage detected" alert if a blockage is detected within the negative pressure circuit when performing any of the verification loop 700, leak loop 800, blockage loop 900 and/or issue identification loop 1000 using the NPWT system monitoring logic 154.

Operation of NPWT System

To initiate NPWT treatment using the NPWT system 100, valve 132 is closed and pump 120 is operated to draw a vacuum within the negative pressure circuit by causing airflow through filter 128 in a first direction (such as, e.g., illustrated by the arrows of FIG. 2). As also illustrated by the arrows of FIG. 2, under normal operating conditions, the negative pressure circuit fluidly couples the wound site 114 to the canister 106, causing air to be removed from the wound site 114 and thus allowing a vacuum to be drawn at the wound site 114. Because the wound site 114 and canister 106 are fluidly connected, the negative pressure at the wound site 114 equilibrates to the pressure within the canister 106, such that the pressure at the wound site 114 is substantially the same as the pressure within the canister 106. Thus, under normal operating conditions, a desired, predetermined pressure may be applied to the wound site 114 by operating the pump 120 until a pressure within canister 106 is determined to have reached the predetermined negative pressure (as determined, e.g., by a pressure reading obtained by pressure sensor 130).

During operation of the NPWT system 100, it may be desired to partially or entirely purge the vacuum applied to the negative pressure circuit. As illustrated by the arrows of FIG. 3, according to various arrangements, the increase of pressure within the negative pressure circuit may be effectuated by opening valve 132 to allow airflow from the environment around therapy device 102 to enter conduit 126 and fill the vacuum within the negative pressure circuit. The airflow from conduit 126 into canister 106 and other volumes within the negative pressure circuit may pass through filter 128 in a second direction, opposite the direction, as shown in FIG. 3.

As will be understood, the NPWT system 100 system may encounter a number of variables or situations that impair the ability of the NPWT system 100 to maintain a wound site 114 at a target treatment pressure as intended.

Figure 5:
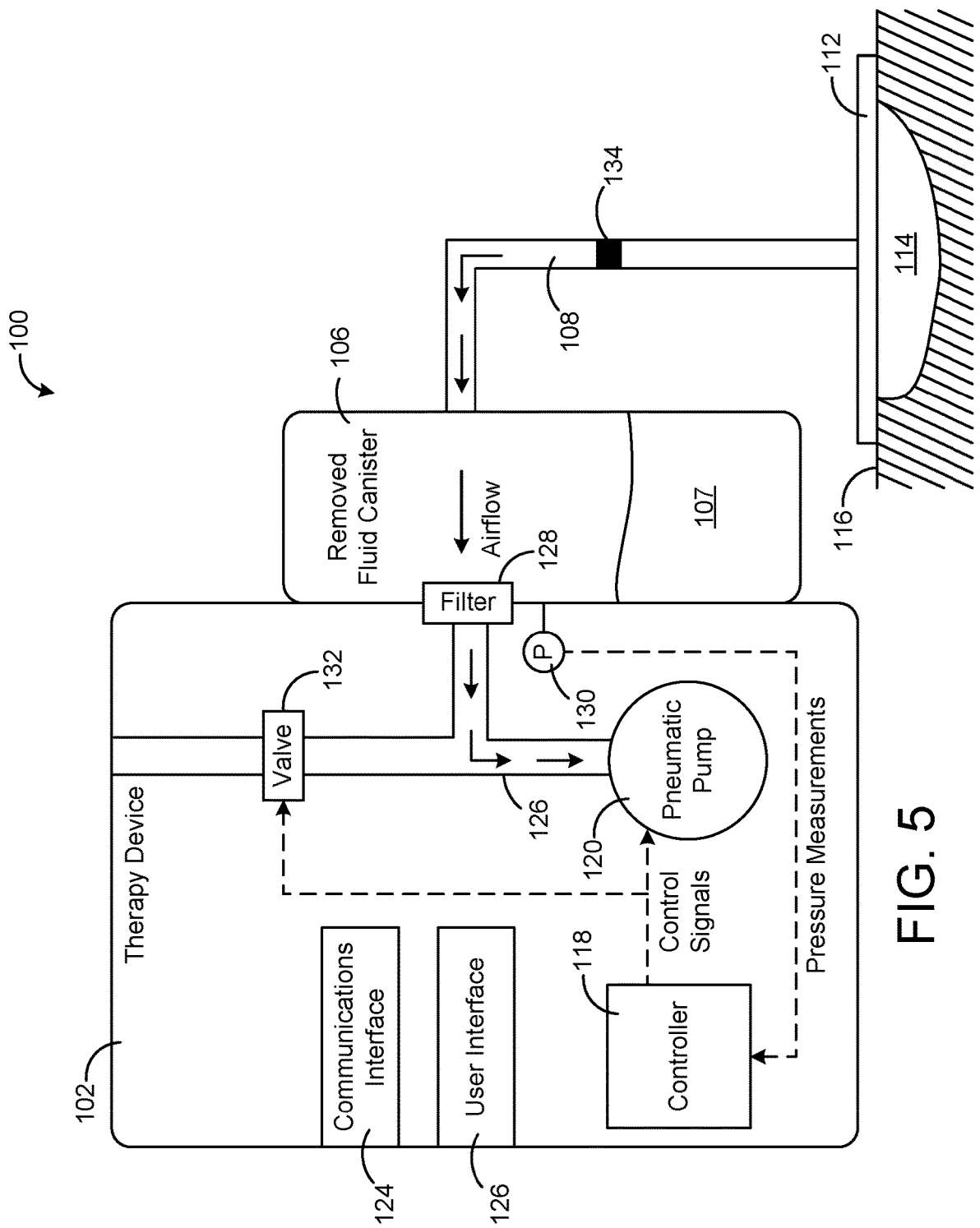
FIG. 5 is a block diagram illustrating the operation of the therapy device of FIG. 1 in the presence of a blockage, according to an exemplary embodiment.

For example, as shown in FIG. 5, in some scenarios, the NPWT system 100 may experience an obstruction, such as, e.g. a blockage 134 occluding an interior of the conduit 108, which may result in the pump 120 failing to draw a vacuum sufficient to achieve the target treatment pressure at the wound site 114. As will be understood, the obstruction may also, or alternatively, be caused by a restriction applied to an external portion of the conduit 108 such as, e.g. a kink in the conduit, a clamp applied to the conduit 108 that has been inadvertently left in a closed configuration, etc. and/or a restriction occurring in any other portions of the negative pressure circuit (e.g. wound dressing 112 inlet, canister 106).

As illustrated in FIG. 5, in the event of a blockage 134, the fluid communication between the canister 106 and the wound site 114, as well as the ability of the pressure at the wound site 114 to equilibrate to the pressure within the canister 106, is prevented or restricted. Thus, as illustrated by the arrows in FIG. 5, although the operation of pump 120 to draw a vacuum results in air being removed from the upstream portion of the negative pressure circuit (i.e. the portion of the negative pressure circuit defined between the pump 120 and the blockage 134), the blockage 134 limits or prevents the flow of air out from the downstream portion of the negative pressure circuit (i.e. the portion of the negative pressure circuit defined between the blockage 134 and the wound site 114).

Because of the inability (or restricted ability) of air to flow out from the downstream portion of the negative pressure circuit during operation of the pump 120, as well as the inability (or restricted ability) of the pressure within the downstream portion of the negative pressure circuit to equilibrate with the pressure within the upstream portion of the negative pressure circuit, the operation of the pump 120 to draw a vacuum may result in a difference between the pressure at the wound site 114 and the pressure within the canister 106. Because the attainment of target treatment pressure within the canister 106 in such a blockage scenario is not necessarily indicative of the pressure at the wound site 114 also being at the target treatment pressure, the operation of the pump 120 based on the monitored pressure within the canister 106 may fail to achieve the target treatment pressure at the wound site 114.

Figure 6:
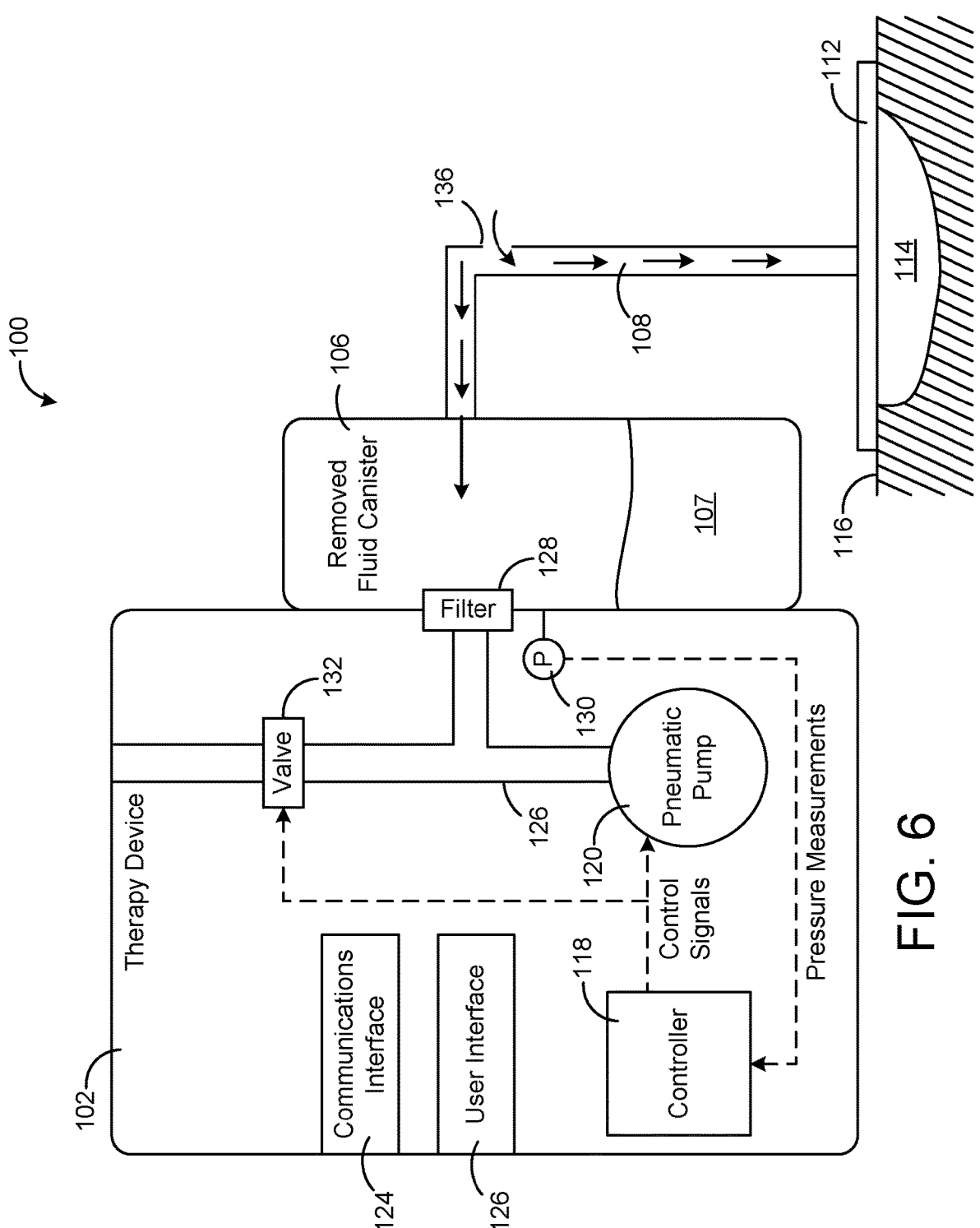
FIG. 6 is a block diagram illustrating the operation of the therapy device of FIG. 1 in the presence of a leak, according to an exemplary embodiment.

Referring to FIG. 6, another scenario which may impair the ability of the NPWT system 100 to maintain a wound site 114 at a target treatment pressure as intended is illustrated. In contrast to the blockage scenario illustrated in and described with reference to FIG. 5 (in which the NPWT system 100 may fail to attain the target treatment pressure at the wound site 114), in the leakage scenario illustrated in FIG. 6, the wound site 114 may initially be subject to the target treatment pressure. However, a leak 136 in the negative pressure circuit through which air from the ambient environment may flow into the negative pressure circuit (such as, e.g., illustrated by the arrows of FIG. 6) may prevent the wound site 114 from being maintained at the target treatment pressure for the intended period of time desired for NPWT treatment.

As will be understood, the increase in pressure within the negative pressure circuit caused by flow of air into the negative pressure circuit through the leak 136 is distinct from, and in addition to, the normal, gradual increase in pressure that normally occurs within the negative pressure circuit as a result of pressure decay. As will also be understood, although the leak 136 is illustrated as occurring in the conduit 108, the leak 136 may occur in any other components defining the negative pressure circuit (e.g. a hole in the canister 106, a tear in the wound dressing 112, etc.) and/or the connections between any of the components of the negative pressure circuit (e.g. impaired seal between the patient's skin 116 and wound dressing, an improperly attachment between the conduit 108 and canister 106, etc.).

Method of Use

Referring to FIGS. 7-10, methods for monitoring and troubleshooting the operation of the NPWT system 100 are shown according to various embodiments. As described, in contrast to existing methods and systems for detecting a blockage in a NPWT therapy device which rely on additional structural components to provide the blockage-detecting capabilities (such as, e.g. additional sensors placed at the wound site, an additional conduit extending from the wound site, etc.), the method described in FIGS. 7-10 allows for detection of a blockage in the NPWT system 100 to include minimal structural components, such as only a single pressure sensor and a single conduit 108 extending between the therapy device 102 and wound dressing 112.

As will be described in more detail below, the various methods described with reference to FIGS. 7-10 below allow the proper operation of the NPWT system 100 to be verified at one or more times prior to or during the use of the NPWT system 100 to provide NPWT treatment. According to various embodiments, the proper operation of the NPWT system 100 as assessed using the one or more processes described with reference to FIGS. 7-10 is based on the comparison of an observed dynamic pressure response within the negative pressure circuit during various points during the operation of the NPWT system 100 to a dynamic pressure response model representative of an expected dynamic pressure response of a properly functioning NPWT system 100 operating under similar conditions.

Figure 7:
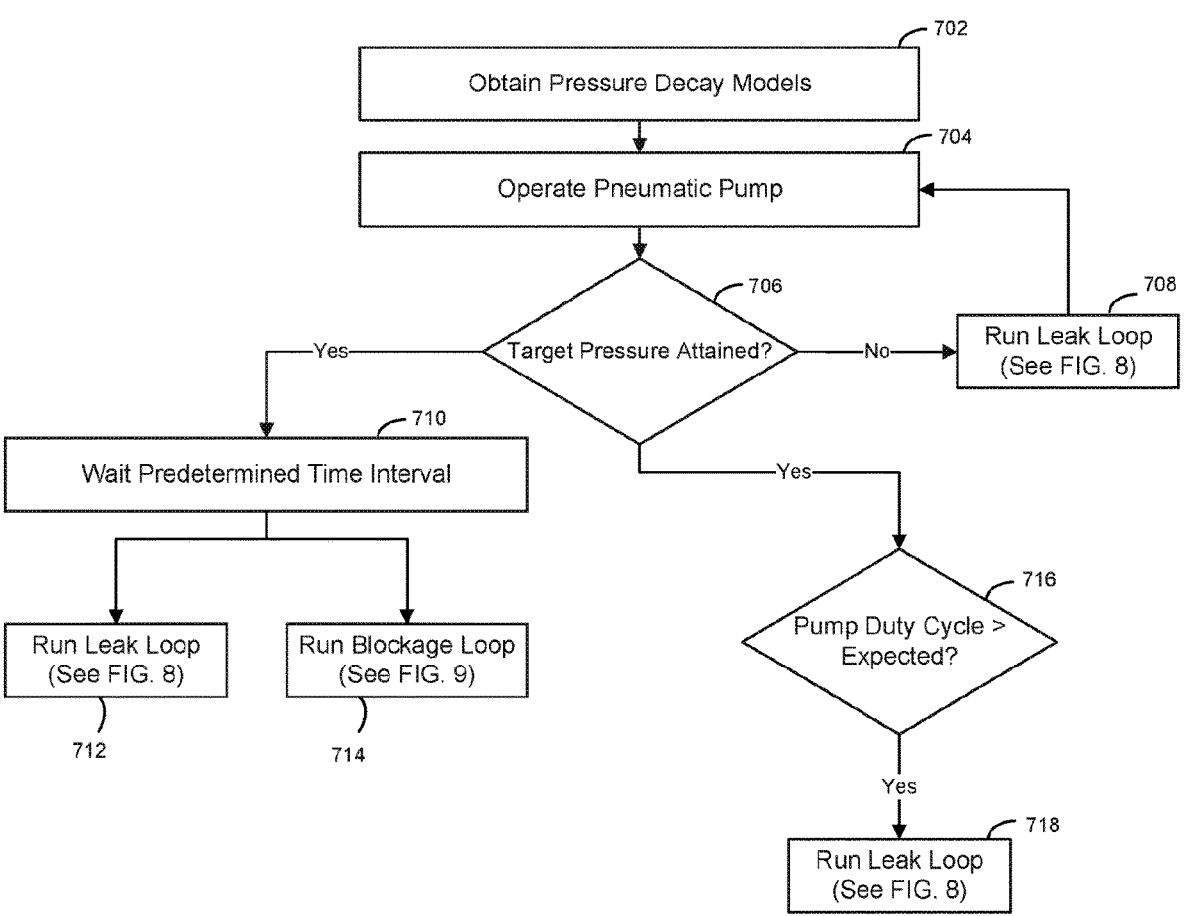
FIG. 7 is a flowchart of a process for monitoring and verifying the proper operation of a wound therapy system, according to an exemplary embodiment.

Referring now to FIG. 7, a flowchart of a verification loop 700 for monitoring and troubleshooting the operation of a wound therapy system is shown, according to an exemplary embodiment. As noted above, (and as will be described in more detail below), according to various embodiments, at one or more steps of the verification loop 700, a dynamic pressure response of the negative pressure circuit to the purging of the negative pressure circuit is monitored and compared to an expected pressure response to determine whether a blockage and/or leak may be present in the NPWT system 100.

Accordingly, at step 702 one or more pressure decay models are obtained. In general, each pressure decay model represents the dynamic pressure response of a negative pressure circuit defined by a particular set of parameters to a pressure stimulus. As these pressure decay curves may vary based on various parameters, such as, e.g. an initial pressure within the negative pressure circuit, the volume of the negative pressure circuit, the leak rate of the valve 132, etc., the pressure decay models obtained 702 obtained at step 702 desirably include pressure decay models representative of a variety of various volumes, initial pressures, leak rates, etc.

As will be understood, pressure decay models obtained at step 702 may be obtained from any number of sources. According to some embodiments, the pressure decay models are existing models stored by the memory 144 of the controller 118. In some embodiments, the pressure decay models are obtained from an external source. In yet other embodiments, the pressure decay models may be generated by the NPWT system 100 according to any number of different protocols for generating such dynamic pressure response data.

According to one such embodiment, the protocols that may be used to generate the pressure decay data at step 702 may be based on the methods disclosed in U.S. Patent Application No. 62/650,132 filed Mar. 29, 2018, titled WOUND THERAPY SYSTEM WITH WOUND VOLUME ESTIMATION, which is herein incorporated by reference in its entirety.

At step 704, the pump 120 is operated to draw a vacuum within the negative pressure circuit so as to attain a desired target pressure within the negative pressure circuit (and in particular, a target pressure desired at the wound site 114). According to some embodiments, the operation of the pump 120 at step 704 may occur immediately following an initial set-up of the NPWT system 100 (e.g. application of the wound dressing 112 to the wound site 114, connection of the conduit 108 to the canister 106, etc.), with the remaining steps of the verification loop 700 being used to verify the proper and correct set-up of the NPWT system 100 prior to an initial use of the NPWT system 100 to provide NPWT treatment. In other embodiments, the operation of the pump 120 at step 704 may occur at any point during an existing NPWT treatment session using the NPWT system 100. As will be understood, in such scenarios, the operation of the pump at step 704 may be based on. e.g., a user initiated request to run the verification loop 700, a reoccurring schedule for running the verification loop 700, etc.

At step 706, it is determined whether the target pressure within the negative pressure circuit has been reached. The target pressure may correspond to any desired predetermined pressure, which may be the same or different from a target pressure used when operating the NPWT system 100 to provide NPWT treatment. According to various embodiments, the target pressure will desirably correspond to a target pressure for which pressure decay data has been obtained at step 702. The determination of whether the negative pressure circuit is at the target pressure may be determined in any desired manner, such as, e.g., based on a pressure reading of the pressure within the canister 106 obtained by pressure sensor 130.

If, at step 706, it is determined that the target pressure within the negative pressure circuit has not been attained, according to some embodiments, a leak loop 800 (as described in more detail below with reference to FIG. 8) may optionally be run at step 708 to determine whether the inability to achieve the target pressure within the negative pressure circuit is attributable to a leak in the negative pressure circuit. If such a leak is detected, the leak is repaired, and the pump continues to run at 704 until the target pressure within the negative pressure circuit has been reached.

As will be understood, in some embodiments, the determination at step 706 that the target pressure has not been attained within the negative pressure circuit may be attributable to insufficient time having passed since the initial operation of the pump 120 at step 704. Accordingly, in such a situation, running the leak loop 800 at step 708 may indicate that there is no leak, with the pump continuing to be run at step 704. In some embodiments, an optional alarm may be generated to the user in the event that the steps of determining that the target has yet to be attained (i.e. step 706) and determining that there is no leak (i.e. step 708) have been performed for a predetermined number of cycles, so as to alert the user to one or more possible issues with the NPWT system 100 (such as, e.g., an issue with the operation of the pump, an incorrect target pressure having been entered, etc.) that may be preventing the attainment of the target pressure within the negative pressure circuit.

According to some embodiments, following the determination at step 706 that the target pressure has been attained, a timer may be initiated at step 710 for a predetermined time interval. According to some embodiments, the timer is set/initiated automatically by the controller 118 in response to the determination at step 706 that the target pressure within the negative pressure circuit has been attained. In other embodiments, the timer may be set manually by a user. Following the expiration of the timer step at step 710, according to some embodiments, one or both of blockage loop 900 (detailed in more description with reference to the FIG. 9 below) and/or leak loop 800 may be run at step 712 and/or step 714, respectively.

According to some embodiments, the timer set at step 710 may be a single timer, with the verification loop 700 alternating between running the leak loop 800 and the blockage loop 900 subsequent to the expiration of the timer at step 710 (e.g., after completing blockage loop 900, steps 702-710 are repeated, with the expiration of the timer at step 710 resulting in the leak loop 800 being run). In other embodiments, the timer set at step 710 may comprise two distinct timers, with the expiration of the first timer resulting in the running of the blockage loop 900 at step 712 and the expiration of the second timer resulting in the running of the leak loop 800 at step 714. In yet other embodiments, step 710 of waiting the predetermined time set by the timer may altogether be omitted (or, the timer predetermined time may be set to zero), with the running of the leak loop 800 at step 714 and/or the blockage loop 900 at step 712 being determined based on one or more of, e.g., a user input request to run one or both of the blockage loop 900 and/or leak loop 800, a predetermined schedule based on the overall operation of the NPWT system 100, etc.

As will be understood, the timer may be set for any desired interval of time at step 710. Advantageously, a lower limit of the time interval set by the timer at step 710 corresponds to a minimum time that would be required to detect deviations from expected pressure decay behavior when running the leak loop 800 and/or the blockage loop 900, so as to ensure that any potential leaks and/or blockages of the NPWT system 100 are not missed. An upper limit of the time interval set by the timer at step 710 advantageously corresponds to a time interval that is less than the expected time that it would take for the target pressure to decay to ambient pressure based on the data obtained at step 702 for a pressure and volume corresponding to the target pressure and volume of the negative pressure circuit. Additionally, in some embodiments, the upper limit of the time interval may be selected so as to minimize any interference with the use of the NPWT system 100.

As noted above, even in the absence of a leak, an initial desired treatment pressure attained within the negative pressure circuit gradually decays over time. Accordingly, in some embodiments, the pump 120 may be configured to periodically be operated to draw an additional vacuum in the negative pressure circuit in an attempt to offset the pressure decay within the negative pressure circuit, and thereby maintain a constant desired treatment pressure at the wound site 114 at a the wound site. As will be understood, the greater the rate of pressure decay within the negative pressure circuit, the greater the duty cycle of the pump 120 (i.e. the number of times the pump 120 is operated) that will be needed to maintain the constant desired treatment pressure.

Accordingly, as shown at step 716, in some embodiments, the duty cycle of the pump 120 may be monitored and compared against a threshold duty cycle representative of the frequency with which the pump 120 operates to maintain a constant pressure at the wound site 114 under normal operating conditions. As leaks are among the various reasons that a pump duty cycle may exceed the expected threshold (as a result of the pump 120 having to be run more frequently to offset the increased pressure caused by the leak) in response to determining that the expected duty cycle threshold has been exceeded at step 716, the leak loop 800 may be performed at step 718 to determine whether the determined increased duty cycle may be attributed to a leak in the NPWT system 100.

Figure 8:
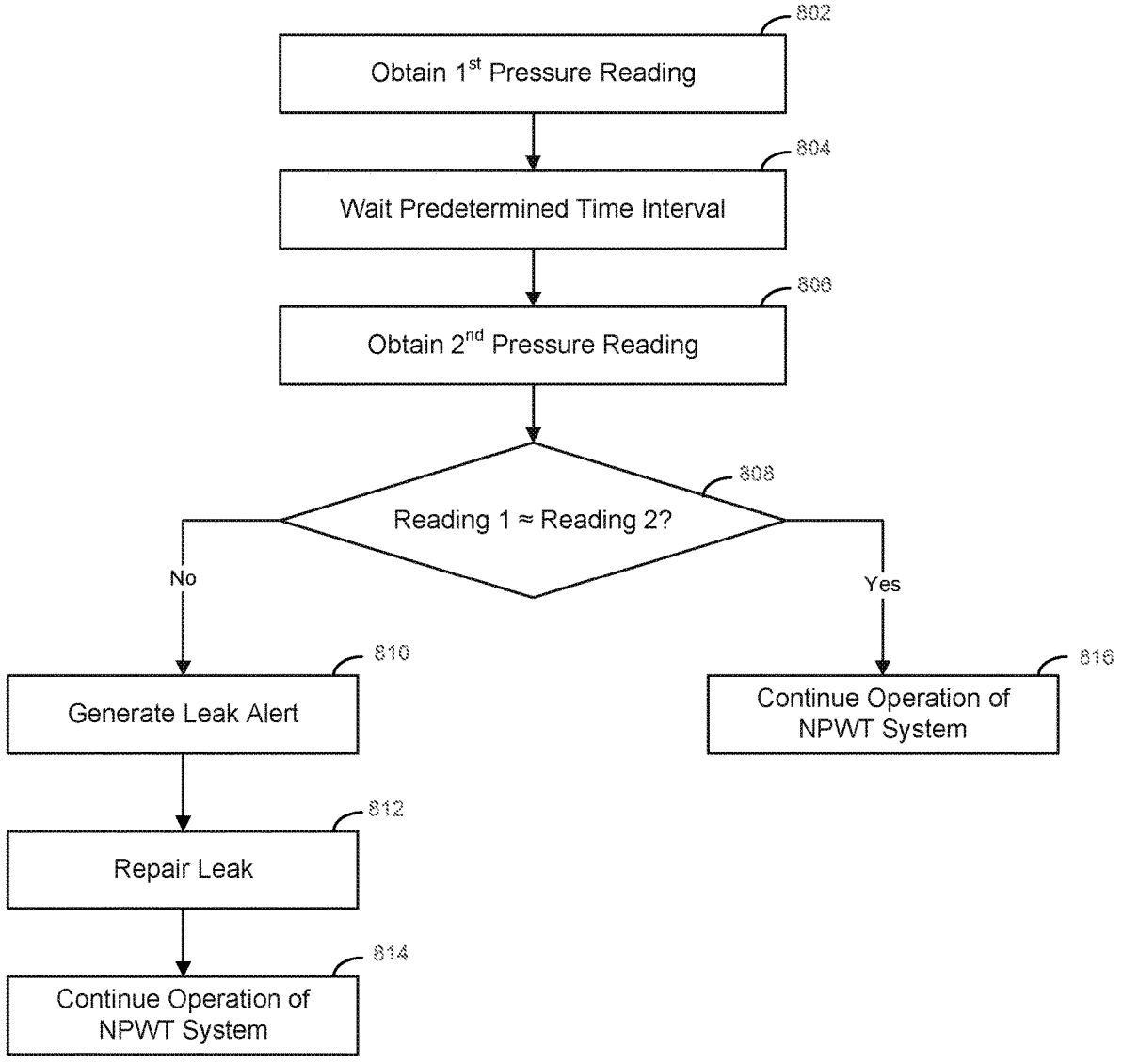
FIG. 8 is a flowchart of a process for detecting a leak within a wound therapy system, according to an exemplary embodiment.

Referring to FIG. 8, one embodiment of a leak loop 800 is illustrated. As will be understood, according to various embodiments, the leak loop 800 may be performed any number of times and on either a scheduled or unscheduled basis as desired. Accordingly, in some embodiments the leak loop 800 may be run without first determining whether the pump duty cycle exceeds a threshold at step 716 and/or without being dependent on the expiration of the predetermined time at step 710 of the verification loop 700.

As shown in FIG. 8, at step 802, a first pressure reading of the pressure within the negative pressure circuit is obtained. The determination of pressure within the negative pressure circuit may be determined in any desired manner, such as, e.g., based on a pressure reading of the pressure within the canister 106 obtained by pressure sensor 130. As will be understood, according to some embodiments, the leak loop 800 may be initiated concurrent with the operation of the pump 120 to attain the desired target pressure within the negative pressure circuit, in which case the pressure reading obtained at step 802 would correspond to the target pressure attained within the negative pressure circuit. According to some embodiments in which the leak loop 800 is run as part of the verification loop 700 of FIG. 7, the first pressure reading obtained at step 802 may correspond to the target pressure has been attained at step 704 of the verification loop 700.

At step 804, a leak timer is set. The timer may be set for any desired interval of time. Advantageously, a lower limit of the time interval set by the timer corresponds to a minimum time that would be sufficient to detect deviations from expected pressure decay behavior when running the leak loop 800, so as to ensure that the effects of any potential leaks in the NPWT system 100 on the pressure decay within the negative pressure circuit are not missed. An upper limit of the time interval set by the timer advantageously corresponds to a time interval that is less than the expected time that it would take for a pressure corresponding to the first pressure reading obtained at step 802 to decay to ambient pressure based on the data obtained at step 702 for a pressure and volume corresponding to the target pressure and volume of the negative pressure circuit. Additionally, in some embodiments, the upper limit of the time interval may be selected so as to minimize any interference with the use of the NPWT system 100.

Once the leak timer set at step 804 has been determined to have expired, a second pressure reading of the pressure within the negative pressure circuit is obtained at step 806. At step 808, the first pressure reading obtained at step 802 is compared to the second pressure reading obtained at step 806. At step 810, a leak alert is generated in response to the determination at step 808 that the two readings are not substantially the same as one another. At step 812, the leak may be repaired, following which at step 814 operation of the NPWT system 100 is continued. Alternatively, if the two readings are determined to be substantially the same as another at step 808, at step 816, operation of the NPWT system 100 may be continued. According to some embodiments, the first and second pressure readings may be determined to be substantially the same as one another at step 808 if the difference between the first pressure reading obtained at step 802 and the second pressure reading obtained at step 806 is between approximately 0 percent and approximately ±15 percent, and more specifically between approximately 0 percent and approximately ±5 percent. As will be understood, according to other embodiments, other suitable ranges may be used in defining the first pressure reading obtained at step 802 and the second pressure reading obtained at step 806 as being substantially similar to one another. As will be understood, according to various embodiments, the suitable range for the difference by which it is determined at step 808 if the first pressure reading obtained at step 802 and the second pressure reading obtained at step 806 are substantially similar may be based on the time interval set at step 804. In some such embodiments, the suitable range used at step 808 may be greater in embodiments in which a greater time interval is waited at step 804.

Figure 9:
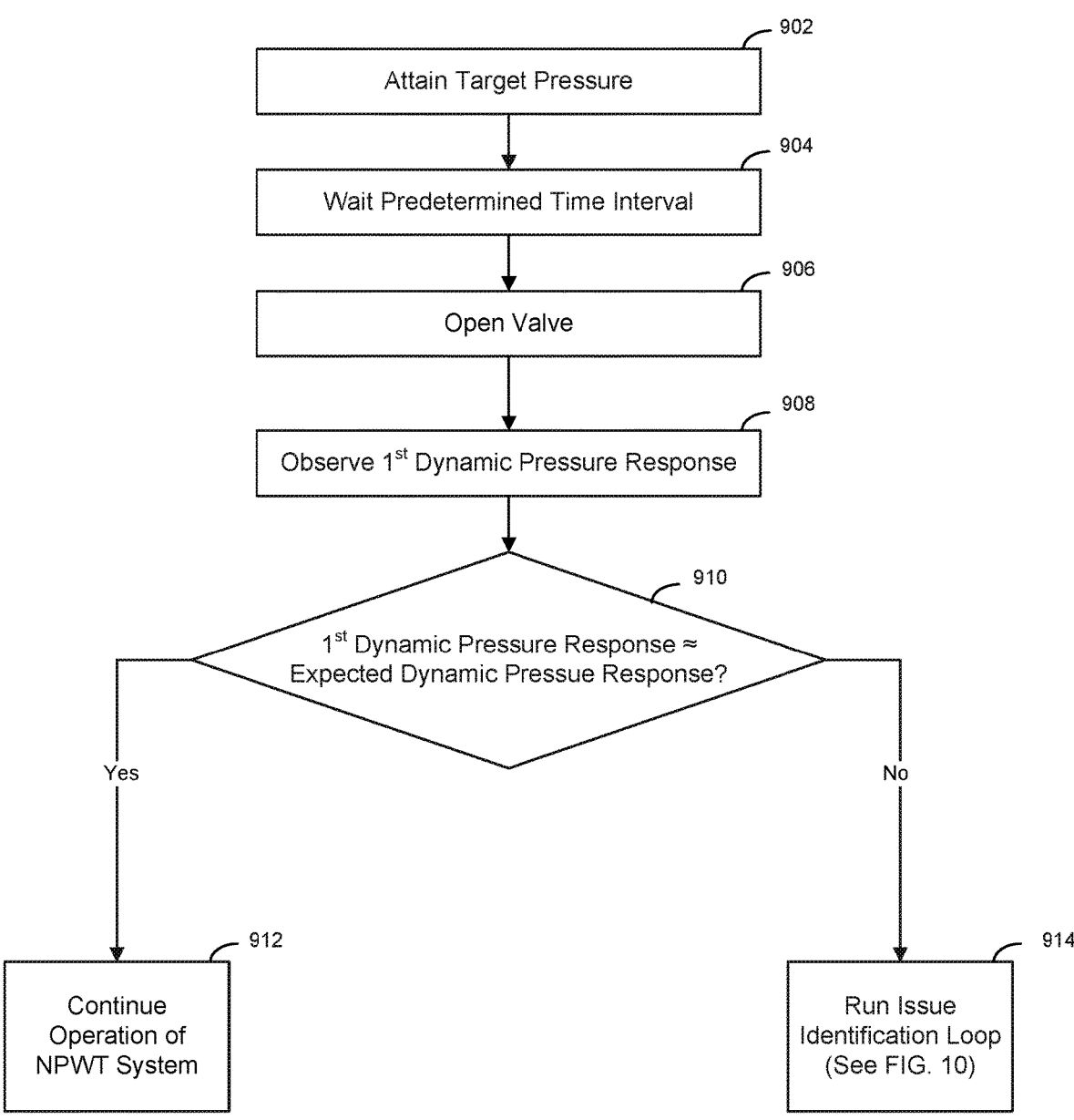
FIG. 9 is a flowchart of a process for detecting an issue in the operation of a wound therapy system, according to an exemplary embodiment.

Turning to FIG. 9, a blockage loop 900 according to one embodiment is described. At step 902, a target pressure is attained within the negative pressure circuit. The target pressure attained at step 902 may be any desired pressure, which may be the same or different from the target pressure that is used during used of the NPWT system 100 to provide NPWT treatment. In some embodiments (such e.g., embodiments in which the blockage loop 900 is performed as step 712 of the verification loop), the target pressure may have been previously attained prior to the commencement of the blockage loop 900, in which situation step 902 is omitted.

At step 904, a timer is set for a predetermined time interval. In embodiments in which the blockage loop is being run as step 712 of the verification loop 700, the time period that is allowed to elapse at step 904 may be the same as the time interval waited at step 710 of the verification loop 700, or may be in addition to the time interval waited at step 710 of the verification loop 700. The considerations relevant to the selection of the time interval may be similar to those used in the selection of a time interval that have been described previously, e.g., with reference to the selection of a time interval at step 710 of the verification loop 700.

Upon the expiration of the time interval at step 904, the valve 132 is opened at step 906 to allow air from the ambient environment to flow into the negative pressure circuit. As will be understood, according to other arrangements, any other number of manners of purging the negative pressure circuit in a controlled manner (i.e. in which the rate of flow of air into the negative pressure circuit may reliably be accounted for) may be used at step 906 in addition to (or as an alternative to) the opening of a valve 132. According to various embodiments, the valve 132 may defined by a calibrated leak that allows for a controlled rate of air to flow into the negative pressure circuit to equilibrate the negative pressure within the negative pressure circuit. In some embodiments, the valve 132 may comprise one or more calibrated leaks. As will be understood, although the valve 132 is shown in FIGS. 1-3 as being defined within the therapy device 102, according to other embodiments, the valve 132 may alternatively, or additionally, be provided by the canister 106 and/or the conduit 108.

The dynamic pressure response to the opening of the valve 132 at step 906 is monitored at step 908. As will be understood, the monitoring of the increasing pressure within the negative pressure circuit at step 908 may be performed in any number of manners, including, e.g. monitoring the changes in pressure within the canister 106 as measured by pressure sensor 130. The monitoring of the pressure decay within the negative pressure circuit at step 908 continues until it has been determined (e.g., via the measurement of pressure within the canister 106 using pressure sensor 130) that the pressure within the removed fluid circuit has reached a predetermined threshold pressure, such as, e.g. a pressure equal to that of the ambient environment. As will be understood, the predetermined threshold pressure may be any pressure that is greater (i.e. less negative) that an initial target pressure attained within the negative pressure circuit prior to the opening of the valve at step 902.

At step 910 the pressure decay within the negative pressure circuit as observed during step 908 is compared against model pressure decay data obtained at step 704 for a model decay curve that corresponds to the parameters defining the negative pressure circuit (e.g. initial target pressure within the negative pressure loop, the volume of the negative pressure loop, the size/rate of flow ratings of the valve, the length of time during which the valve was opened, etc.) to determine whether the observed pressure decay at step 908 is substantially the same as the expected pressure decay based on the model pressure decay data. According to some embodiments, observed pressure decay at step 908 may be determined to be substantially the same as the expected data if the difference between the measured and expected pressure decay is between approximately 0 percent and approximately ±15 percent, and more specifically between approximately 0 percent and approximately 5 percent.

If it is determined at step 910 that the pressure decay observed at step 908 is substantially similar to the expected pressure decay, at step 912 the NPWT system 100 is identified as operating as intended, and the operation of the NPWT system 100 may be continued as originally intended. In contrast, if it is determined at step 910 that the pressure decay observed at step 908 is not substantially similar to the expected pressure decay, at step 914, an issue identification loop 1000 may be run to identify the source of the discrepancy between the observed pressure decay at step 908 with expected pressure decay determined at step 910.

Figure 10:
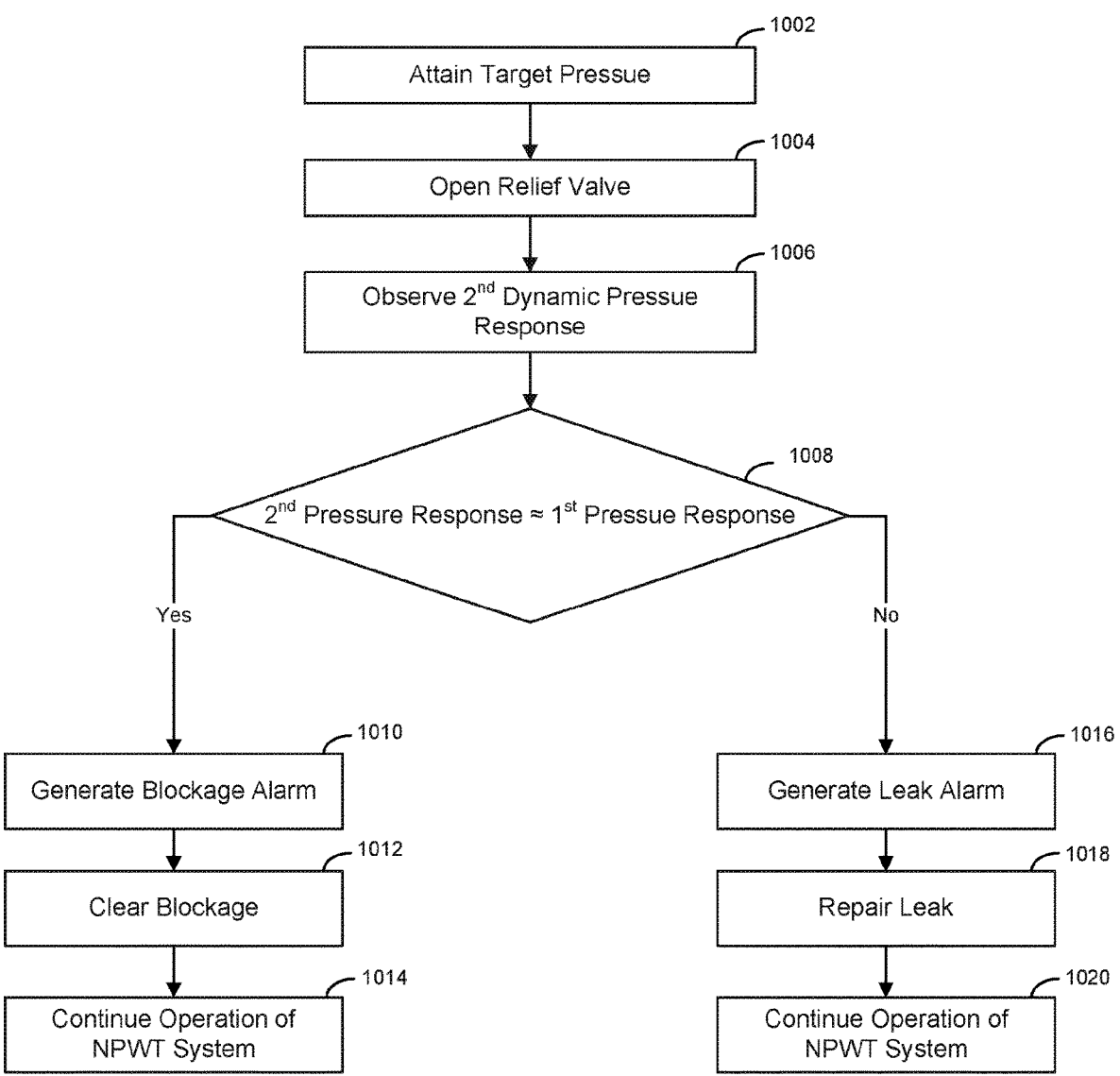
FIG. 10 is a flowchart of a process for identifying the source of an issue in the operation of a wound therapy system, according to an exemplary embodiment.

Referring to FIG. 10, an issue identification loop 1000 according to one embodiment is illustrated. As will be understood, although the determination at step 910 that the observed pressure decay of step 908 is not substantially similar to the expected pressure decay may be sufficient to alert a user to an issue with the NPWT system 100, this determination alone may not be enough to allow the user to easily determine the underlying source of the issue with the NPWT system 100.

At step 1002, the pump 120 is operated to apply the same target pressure to the negative pressure circuit as was applied to the negative pressure circuit during step 902 of the blockage loop (which, if the issue identification is being run in response to the running of the verification loop 700 of FIG. 7, is the same target pressure applied to the negative pressure circuit at step 704). In contrast the predetermined time waited at step 904 (or, if the issue identification loop 1000 is being run in response to the running of the verification loop 700 of FIG. 7, the time interval waited at step 710) following the attainment of the target pressure within the negative pressure circuit, at step 1004, the valve is opened 128 immediately following the target pressure being reaching within the negative pressure circuit. The opening of the valve 132 at step 1004 (or the purging of the negative pressure circuit using other means) is carried out in a manner identical (e.g. same degree of opening of the valve 132, same duration of time for which the valve 132 is opened, etc.) to the manner in which the valve 132 or other purge mechanism was operated at step 906 of the blockage loop 900.

At step 1006 the dynamic pressure response in response to the opening of the valve 132 at step 1004 is monitored as the pressure within the negative pressure circuit increases to the threshold pressure (e.g. ambient pressure). As will be understood, the monitoring of the increasing pressure within the negative pressure circuit at step 1006 may be performed in any number of manners, including. e.g. monitoring the changes in pressure within the canister 106 as measured by pressure sensor 130. The monitoring of the pressure decay within the negative pressure circuit at step 1006 continues until it has been determined (e.g., via the measurement of pressure within the canister 106 using pressure sensor 130) that the pressure within the removed fluid circuit has reached a predetermined threshold pressure that is the same as the predetermined threshold pressure reached at step 908 of the blockage loop 900.

At step 1008, the dynamic pressure response observed at step 1006 is compared to the dynamic pressure response observed at step 908 to determine whether the second pressure decay reading obtained at step 1006 is substantially the same as the first pressure decay reading obtained at step 908 of the blockage loop 900. According to various embodiments, the first reading and second reading may be considered substantially similar to one another at step 1008 if the dynamic pressure response observed at step 1006 and the dynamic pressure response observed at step 908 are determined to be between 0 percent and approximately ±15 percent, and more specifically between approximately 0 percent and approximately ±5 percent of one another. As will be understood, according to other embodiments, other suitable ranges may be used in defining the dynamic pressure response observed at step 1006 and the dynamic pressure response observed at step 908 as being substantially similar to one another.

As noted above, a certain degree of pressure decay is anticipated within the negative pressure circuit over time. Accordingly, the determination of whether the two reading are substantially the same at step 1008 may in some arrangements vary based on the time interval set with the timer at step 904 of the blockage loop 900 (which, as noted above, in some embodiments in which the blockage loop 900 is being performed at step 712 of the verification loop 700 may be equal to the time interval waited at step 710). Accordingly, in some embodiments, the acceptable degree of difference and/or an acceptable absolute difference between the first dynamic pressure response observed at step 908 and the second dynamic pressure response observed at step 1006 that would be considered as being substantially similar at step 1008 may additionally, or alternatively, be based on the time interval waited at step 904 of the blockage loop 900.

At step 1010 a blockage alarm is generated in response to a determination at step 1008 that the dynamic pressure response obtained at step 1008 is substantially the same as the dynamic pressure response obtained at step 908. In particular, a blockage 134 in the negative pressure circuit reduces the effective volume of the negative pressure circuit. Because smaller volumes (e.g., a negative pressure circuit with a blockage 134) require less time to be purged of negative pressure than larger volumes (e.g., the same negative pressure circuit without the blockage), a negative pressure circuit with a blockage would be expected to exhibit a different pressure decay curve that varies (i.e. one that reaches the predetermined threshold pressure in a lesser time) from a pressure decay curve of a negative pressure circuit without a blockage under similar conditions. However, under similar purge conditions, the pressure decay curves of negative pressure circuits having the same volume and subject to the same initial target pressure would be substantially similar to one another, irrespective of the amount of time that may have passed between the attainment of the target pressure within negative pressure circuit and the purging of the negative pressure circuit. At step 1012, the blockage may be cleared, following which, at step 1014, normal operation of the NPWT system 100 may resume.

At step 1016 a leak alarm is generated in response to a determination at step 1008 that the dynamic pressure response observed at step 1008 is not substantially the same as the dynamic pressure response observed at step 908. In particular, under a leak condition, air that is introduced into the negative pressure circuit through the leak 136 results in the pressure in the negative circuit decaying (i.e. becoming more positive) at a faster rate than would be expected under normal operating conditions, with the pressure within the negative pressure circuit increasing as more air is introduced into the negative pressure circuit through the leak 136. Thus, the longer the time waited between the attainment of a target pressure within the negative pressure circuit and the purging of the negative pressure circuit, the lower the pressure within the negative circuit will be at the point at which the valve 132 is opened to purge the negative pressure circuit. As a negative pressure circuit having a higher (i.e. more negative) initial target pressure will require more time to achieve a threshold pressure that would a negative pressure circuit of the same volume having a lower (i.e. less negative) initial target pressure, the dynamic pressure response within the negative pressure observed following the opening of the valve 132 in a situation in which a predetermined period of time was allowed to pass between the attainment of the target pressure and the purging of the negative pressure circuit will vary from the dynamic pressure response within the negative pressure observed following the opening of the valve 132 in a situation in which the purging of the negative pressure circuit occurred immediately after (or in less time than the predetermined time) following the attainment of the target pressure. At step 1018, the leak may be repaired, following which at step 1020 normal operation of the NPWT system 100 may resume.

As will be understood, according to some embodiments, a blockage 134 in the negative pressure circuit may become dislodged by itself during the steps of drawing a vacuum in the negative pressure circuit and/or purging the negative pressure within the negative pressure circuit. In such embodiments, a discrepancy between the observed dynamic pressure responses during the blockage loop 900 and/or issue identification loop 1000 may be determined at step 1008 as not being substantially similar to one another. Accordingly, in some embodiments, prior to generating the leak alarm at step 1016 and/or in the event that a leak cannot be found during step 1018, the blockage loop 900 and/or issue identification loop 1000 may be repeated to verify whether the initial discrepancy between the two observed dynamic pressure response determined at step 1008 has been resolved by itself.

As will be understood, in addition to being used to monitor and verify the operation of the NPWT system 100 disclosed herein, the verification loop 700, leak loop 800, blockage loop 900 and/or issue identification loop 1000 described with reference to FIGS. 7-10 may optionally be used with other existing wound therapy systems, allowing such existing NPWT therapy devices formed without blockage and/or leak detecting capabilities to be provided with such capabilities without requiring and physical reconfiguration and/or modification to do so.

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure can be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM. EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures show a specific order of method steps, the order of the steps may differ from what is depicted. Also two or more steps can be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

What is claimed is:

1. A wound therapy system comprising:
a canister configured to contain fluid removed from a wound site;
a conduit having a first end coupled to the canister and a second end operably coupled to the wound site, wherein an interior volume of the conduit is defined by a single lumen providing the only fluid path to the wound site;
wherein an interior volume of the canister and the interior volume of the conduit define a negative pressure circuit;
a pump fluidly operably coupled to the wound site via the conduit and configured to apply negative pressure to the wound site via the negative pressure circuit;
a pressure indicator configured to indicate a pressure within the negative pressure circuit; and
a controller configured to:
store a baseline pressure decay curve from an external model including an estimated volume and leak rate equal to the negative pressure circuit and that is representative of an expected change in pressure within the negative pressure circuit from a first negative pressure to a predetermined threshold pressure over a first period of time;
generate a second pressure decay curve by operating the pump to apply a second applied negative pressure equal to the first negative pressure to the negative pressure circuit and measuring a change in pressure over a second period of time within the negative pressure circuit during which the pressure within the negative pressure circuit increases from the second applied negative pressure to the threshold pressure;
compare the second pressure decay curve to the baseline pressure decay curve; and
generate an alert in response to detecting that a difference between the second pressure decay curve and the baseline pressure decay curve exceeds a predetermined first variance threshold.

2. The wound therapy system of claim 1, wherein, in response to generating the alert, the controller is further configured to:
generate a third pressure decay curve by operating the pump to apply a third applied negative pressure equal to the first negative pressure to the negative pressure circuit and measuring a change in pressure over a third time period within the negative pressure circuit during which the pressure within the negative pressure circuit increases from the third applied negative pressure to the threshold pressure; and
compare the third pressure decay curve to the second pressure decay curve.

3. The wound therapy system of claim 2, wherein the controller is further configured to generate a blockage alarm in response to detecting that the third pressure decay curve is substantially the same as the second pressure decay curve.

4. The wound therapy system of claim 2, wherein the controller is further configured to generate a leakage alarm in response to detecting that a difference between the third pressure decay curve and the second pressure decay curve exceeds a predetermined second variance threshold.

5. The wound therapy system of claim 1, wherein, in response to detecting that the second pressure decay curve is substantially the same as the baseline pressure decay curve, the controller is further configured to, following a predetermined time interval:
generate a third pressure decay curve by operating the pump to apply a third applied negative pressure equal to the first negative pressure to the negative pressure circuit and measuring a change in pressure over a third time period within the negative pressure circuit during which the pressure within the negative pressure circuit increases from the third applied negative pressure to the threshold pressure; and compare the third pressure decay curve to the baseline pressure decay curve.

6. The wound therapy system of claim 1, wherein the baseline pressure decay curve is one of a plurality of baseline pressure decay curves stored by the controller, the controller further comprising a second baseline pressure decay curve generated based on measuring pressure decay within the negative pressure circuit prior to an initial use of the wound therapy system to provide negative pressure therapy to the wound site.

7. The wound therapy system of claim 1, further comprising a calibrated leak in fluid communication with the negative pressure circuit, the calibrated leak configured to allow ambient air to flow into the negative pressure circuit at a known flow rate and increase in pressure within the negative pressure circuit.

8. The wound therapy system of claim 1, wherein the detected difference between the second pressure decay curve and the baseline pressure decay curve comprises at least one of a difference between a slope of the baseline pressure decay curve and a slope of the second pressure decay curve and a difference between the first period of the time and the second period of time.

9. The wound therapy system of claim 8, wherein the first variance threshold is between approximately 5% and approximately 15%.

10. The wound therapy system of claim 4, wherein the detected difference between the third pressure decay curve and the second pressure decay curve comprises at least one of a difference between a slope of the third pressure decay curve and a slope of the second pressure decay curve and a difference between the third period of the time and the second period of time.

11. The wound therapy system of claim 4, wherein the detected difference between the second pressure decay curve and the baseline pressure decay curve comprises at least one of a difference between a slope of the baseline pressure decay curve and a slope of the second pressure decay curve and a difference between the first period of the time and the second period of time.

12. The wound therapy system of claim 1, wherein the baseline pressure decay curve stored by the controller comprises a plurality of volume-specific baseline pressure decay curves, each of the volume-specific baseline pressure decay curves being representative of a change in pressure within a negative pressure circuit defined by a specific volume; the controller further being configured to determine a volume of the negative pressure circuit, wherein the baseline pressure decay curve to which the second decay curve is compared comprises a volume-specific baseline pressure decay curve corresponding to the determined volume of the negative pressure circuit.

13. The wound therapy system of claim 12, wherein the volume of the negative pressure circuit is determined based on an identification by the controller of the interior volume of the canister.

14. The wound therapy system of claim 13, wherein the volume of the negative pressure circuit is further determined based on an identification by the controller of an amount of fluid that has been instilled to the wound site.

\* \* \* \* \*